US006617289B2

(12) United States Patent
Memita et al.

(10) Patent No.: US 6,617,289 B2
(45) Date of Patent: Sep. 9, 2003

(54) METHOD FOR PRODUCING ESTER

(75) Inventors: Michimasa Memita, Amagasaki (JP); Keiji Hirao, Kobe (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 09/977,926

(22) Filed: Oct. 15, 2001

(65) Prior Publication Data
US 2002/0137640 A1 Sep. 26, 2002

(30) Foreign Application Priority Data
Oct. 16, 2000 (JP) ........................ 2000-315799

(51) Int. Cl.[7] .................. C10M 129/74; C07C 69/22
(52) U.S. Cl. .................. 508/485; 252/68; 560/129
(58) Field of Search ................... 560/129; 508/485

(56) References Cited

U.S. PATENT DOCUMENTS

| 4,826,633 A | * | 5/1989 | Carr et al. .................. 508/485 |
| 5,081,280 A | | 1/1992 | Takee et al. |
| 5,290,465 A | * | 3/1994 | Sabahi ........................ 508/465 |
| 5,503,761 A | * | 4/1996 | Ashcraft, Jr. et al. ....... 508/465 |
| 5,705,086 A | | 1/1998 | Ardito et al. |
| 5,707,944 A | * | 1/1998 | Yokouchi et al. ........... 508/485 |
| 5,716,916 A | * | 2/1998 | Shiokawa et al. .......... 508/485 |
| 5,830,833 A | * | 11/1998 | Grasshoff et al. ............ 508/485 |
| 5,895,778 A | * | 4/1999 | McHenry et al. ........... 508/495 |
| 5,976,399 A | * | 11/1999 | Schnur ........................ 252/68 |
| 6,177,387 B1 | * | 1/2001 | Scholsberg et al. ......... 508/485 |
| 6,265,361 B1 | * | 7/2001 | Akiyama et al. ............ 508/462 |
| 6,436,881 B1 | * | 8/2002 | McHenry et al. ........... 508/280 |
| 6,444,626 B1 | * | 9/2002 | McHenry et al. ........... 508/495 |

FOREIGN PATENT DOCUMENTS

| JP | 54-91589 | 7/1979 |
| JP | 54-132502 | 10/1979 |
| JP | 07-45437 | 5/1995 |
| JP | 07-309937 | 11/1995 |
| JP | 2000-508691 | 7/2000 |
| WO | WO 97/08277 | 3/1997 |
| WO | WO 97/39079 | 10/1997 |

* cited by examiner

Primary Examiner—Ellen M. McAvoy
(74) Attorney, Agent, or Firm—Webb, Ziesenheim Logsdon Orkin & Hanson, P.C.

(57) ABSTRACT

The present invention provides a method for producing a high quality ester and an ester obtained by this method. The method includes reacting an alcohol with a carboxylic acid in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester. This ester is useful as ester lubricating base stock for grease, automotive engine oil, and refrigerating machine oil.

13 Claims, No Drawings

METHOD FOR PRODUCING ESTER

BACKGROUND OF THE INVENTION

1. Field of the Invention

The present invention relates to a method for producing an ester that includes a reaction in the presence of a Lewis acid catalyst and a phosphorus-containing reducing agent, and an ester, obtained by the production method. The present invention also relates to ester lubricating base stocks for grease, refrigerating machine oil and automotive engine oil and compositions containing the base stock.

2. Description of the Related Art

Esters are used in a wide range of fields such as cosmetics, pharmaceutical preparations, foods, electronic equipment, printing, and lubrication, etc. In recent years, with technological development in these fields using esters, each field requires esters with suitable qualities. For example, for esters used for grease, durability and anti-evaporation properties at high temperatures are required. For esters used for engine oil, long life and good thermal and oxidative stability are required. For esters used for refrigerating machine oils, high electric insulation properties and heat resistance are required, and it is also required that contaminants or conductive impurities are hardly contained, the acid value and hydroxyl value of the esters are low, and the hydrolytic stability and heat stability at high temperatures of the esters are excellent.

Esters can be obtained by a reaction between a carboxylic acid and an alcohol. In general, the reaction is carried out with an excessive amount of the carboxylic acid in order to obtain esters having a low hydroxyl value. In this esterification reaction, a Brønsted acid such as sulfuric acid, hydrochloric acid, p-toluenesulfonic acid, methanesulfonic acid, or naphthalenesulfonic acid is commonly used as a catalyst. In the esterification reaction using such a Brønsted acid, byproducts tend to be produced. The produced byproducts and the remaining catalyst are removed by purification by means of neutralization with an alkali, adsorption with an adsorbent, steaming, etc., which can be performed alone or in combination. However, it is difficult to sufficiently remove the byproducts and the remaining catalyst, and the remaining byproducts and catalyst are factors that may deteriorate the thermal and oxidative stability of the esters. Thus, there is no ester that satisfies the various requirements.

Japanese Laid-Open Patent Publication Nos. 54-91589 and 54-132502 describe a method for performing esterification in the presence of an acid catalyst such as a Brønsted acid and an ion exchange resin and phosphorous acid, hypophosphorous acid or salts thereof. Japanese Patent Publication No. 7-45437 describes a method for producing esters that includes a process of ester exchange in the presence of a mono-organic tin compound. Although these methods have some effects in that less colored esters can be obtained, the long-time thermal and oxidative stability is still insufficient.

In another example, less colored polyester is produced by adding a stabilizer containing a phosphorus-containing compound, a phenol-containing compound, a thioether-containing compound, an amine compound or the like, as disclosed in Japanese Laid-Open Patent Publication No. 7-309937. However, it is difficult to remove these stabilizers from the reaction product, and the stabilizer that remains in ester acts as an accelerator of deterioration of the ester so that sludge may be produced or discoloring may be caused when used at a high temperature for a long time.

Examples of Japanese Laid-Open Patent Publication No. 2000-508691 include a method using dibutyltin oxide as a catalyst for esterification. However, the ester obtained by this method is colored at high temperatures, and the ester has a high acid value, and, thus, the thermal and oxidative stability of the ester is insufficient. Furthermore, for all the engine oils described in PCT Publication No. WO 97/008277, esters produced in the absence of a catalyst are used as the base stock. The method described therein requires esterification reaction at a high temperature for a long time in the process of producing the esters, so that the esters are thermally deteriorated significantly during the reaction. Therefore, the heat resistance of the ester base stock is not sufficient, and there are problems with regard to the long-term stability.

Base catalysts are also known as catalysts for esterification. For example, N,N'-dicyclohexylcarbodiimide-4-(N,N-dimethylamino) pyridine, triphenyl phosphine-2,2'-dipyridyl sulfide or the like is used. However, when the base catalyst is used, the reaction mixture is colored blackish brown, and thus, high quality esters cannot be obtained.

As described above, there is no method for producing high quality esters that satisfies the requirements of various fields.

SUMMARY OF THE INVENTION

The method for producing an ester of the present invention includes reacting an alcohol with a carboxylic acid and comprises: reacting the alcohol with the carboxylic acid in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester.

In a preferred embodiment, the Lewis acid catalyst is at least one selected from the group consisting of titanium-containing Lewis acid catalysts, tin-containing Lewis acid catalysts, antimony-containing Lewis acid catalysts, germanium-containing Lewis acid catalysts, and zirconium-containing Lewis acid catalysts.

In a preferred embodiment, the alcohol is a neopentyl polyol having 2 to 6 hydroxyl groups, and the carboxylic acid is a monocarboxylic acid having 5 to 10 carbon atoms.

In a preferred embodiment, the alcohol is a neopentyl polyol having 2 to 4 hydroxyl groups, and the carboxylic acid is a monocarboxylic acid having 5 to 12 carbon atoms.

The ester of the present invention is obtained by a process comprising: reacting an alcohol with a carboxylic acid in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

The ester lubricating base stock for grease of the present invention is obtained by a method comprising: reacting a neopentyl polyol having 2 to 6 hydroxyl groups with a monocarboxylic acid having 5 to 10 carbon atoms in the presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

The ester lubricating base stock for refrigerating machine oil of the present invention is obtained by a process comprising: reacting a neopentyl polyol having 2 to 6 hydroxyl groups with a monocarboxylic acid having 5 to 10 carbon atoms in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

The ester lubricating base stock for automotive engine oil obtained by a process comprising: reacting a neopentyl polyol having 2 to 4 hydroxyl groups with a monocarboxylic acid having 5 to 12 carbon atoms in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

In a preferred embodiment, the grease composition comprises the above-mentioned ester lubricating base stock for grease, a thickener, and an antioxidant, and wherein the ester lubricating base stock for grease is contained in a ratio of 10 to 90% by weight.

In a preferred embodiment, the working fluid composition for refrigerating machine oil comprises the above-mentioned ester lubricating base stock for refrigerating machine oil and a hydrofluorocarbon in a weight ratio of 10:90 to 90:10.

The composition for engine oil of the present invention comprises the above-mentioned ester lubricating base stock for automotive engine oil, an anti-wear additive, and an antioxidant, and wherein the ester lubricating base stock for automotive engine oil is contained in a ratio of 5 to 95% by weight.

Thus, the present invention described herein makes possible the advantages of providing a method for producing high quality esters, especially esters having excellent thermal and oxidative stability, and esters obtained by this method; and providing ester lubricating base stocks for grease, automotive engine oil, and refrigerating machine oil that contain the esters and that can be used for a long period of time even under severe use conditions of high speed and high load of recent machines; and compositions containing these base stocks.

DESCRIPTION OF THE INVENTION

Carboxylic Acid

Examples of the carboxylic acid used in the present invention include monocarboxylic acids and polycarboxylic acids. These carboxylic acids can be either saturated or unsaturated carboxylic acids and can be either linear or branched. Preferably, saturated and linear or branched carboxylic acids are used.

Examples of the monocarboxylic acids include valeric acid, isovaleric acid, caproic acid, 2-ethylbutanoic acid, heptanoic acid, 2-methylhexanoic acid, 3-methylhexanoic acid, 4-methylhexanoic acid, 5-methylhexanoic acid, 2,2-dimethylpentanoic acid, 2-ethylpentanoic acid, 3-ethylpentanoic acid, isoheptanoic acid, caprylic acid, 2-ethylhexanoic acid, nonanoic acid, 3,5,5-trimethylhexanoic acid, neononanoic acid, capric acid, neodecanoic acid, lauric acid, myristic acid, palmitic acid, stearic acid, oleic acid, linolic acid, linolenic acid, arachic acid, erucic acid, behenic acid, lignoceric acid, cerotic acid, montanoic acid, melissic acid, and the like.

Examples of the polycarboxylic acids include succinic acid, glutanic acid, adipic acid, pimelic acid, suberic acid, azelaic acid, sebacic acid, undecanedioic acid, dodecanedioic acid, tridecanedioic acid, carboxyoctadecanoic acid, carboxymethyloctadecanoic acid, docosanedioic acid, dimer acid, phthalic acid, isophthalic acid, fumaric acid, maleic acid, trimellitic acid, pyromellitic acid, and the like.

These carboxylic acids can be used alone or in combination.

Alcohol

Examples of the alcohol used in the present invention include monohydric alcohols, polyhydric alcohols and ether compounds that can be obtained by an addition reaction of an alkylene oxide with the alcohol.

Examples of the monohydric alcohols include pentanol, isopentanol, hexanol, cyclohexanol, heptanol, octanol, 2-ethylhexanol, nonanol, 3,5,5-trimethylhexanol, isononanol, decanol, isodecanol, lauryl alcohol, myristyl alcohol, cetyl alcohol, stearyl alcohol, eicosanol, docosanol, tetracosanol, hexacosanol, octacosanol, nonacosanol, melissyl alcohol and the like.

Examples of the polyhydric alcohols include ethylene glycol, propylene glycol, polyalkylene glycols, 1,3-propanediol, 1,4-butanediol, 1,5-pentanediol, 1,6-hexanediol, diethylene glycol, dipropylene glycol, 2,2,4-trimethyl-1,3-pentanediol, spiroglycol, 1,4-phenylene glycol, 1,2,4-butanetriol, 1,2,5-pentanetriol, 1,2,3,6-hexanetetraol, 2-methyl-1,2,4-butanetriol, erythrite, arabitol, sorbitol, mannitol, sorbitan, glycerine, 2-methylpropanetriol, neopentylglycol, 2,2-diethyl-1,3-propanediol, 2-n-butyl-2-ethyl-1,3-propanediol, trimethylolethane, triethylolethane, trimethylolpropane, pentaerythritol, dipentaerythritol, tripentaerythritol, 1,3,5-trihydroxymethylbenzene and the like.

Examples of the alkylene oxide that can be used for the addition reaction include ethylene oxide, propylene oxide, butylene oxide, and the like.

These alcohols can be used alone or in combination.

Lewis Acid Catalyst

Examples of the Lewis acid catalyst used in the present invention include titanium-containing Lewis acid catalysts, tin-containing Lewis acid catalysts, antimony-containing Lewis acid catalysts, zinc-containing Lewis acid catalysts, germanium-containing Lewis acid catalysts, zirconium-containing Lewis acid catalysts, and hafnium-containing Lewis acid catalysts.

Examples of the titanium-containing Lewis acid catalysts include titanium tetramethoxide, titanium tetraethoxide, titanium tetraisopropoxide, titanium tetra-n-butoxide, titanium tetraoctoxide, titanium ethylacetoacetate, octylene glycol titanate, and the like.

Examples of the tin-containing Lewis acid catalysts include monoalkyl tin esters, dialkyl tin esters, monoalkyl tin oxides, dialkyl tin oxides, and the like. As alkyl groups contained in the compounds used as the tin-containing catalysts, linear or branched alkyls having 1 to 12 carbon atoms are preferable. Specific examples of the tin-containing catalyst include monobutyltin mono(2-ethylhexanoate), monobutyltin tris(2-ethylhexanoate), dibutyltin bis(2-ethylhexanoate), stannous 2-ethylhexanoate, dibutyltin diacetate, monobutyltin oxide, dibutyltin oxide, and the like.

Examples of the antimony-containing Lewis acid catalysts include antimony triethoxide, antimony tributoxide, antimony trioxide, and the like.

Examples of the zinc-containing Lewis acid catalysts include zinc chloride, zinc acetate, and zinc carbonate.

Examples of the germanium-containing Lewis acid catalysts include germanium selenide, germanium dioxide, germanium tetrachloride, germanium tetra-n-butoxide, and the like.

Examples of the zirconium-containing Lewis acid catalysts include zirconium tetramethoxide, zirconium tetraethoxide, zirconium tetra-n-propoxide, zirconium tetraisopropoxide, zirconium tetra-n-butoxide, zirconium tetra-t-butoxide, zirconium oxide, zirconium tungstate, zirconium tetra-2-ethylhectoxide, and the like.

Examples of the hafnium-containing Lewis acid catalysts include hafnium tetramethoxide, hafnium tetraethoxide, hafnium tetra-t-butoxide, hafnium tetra-2-ethylhexyloxide, hafnium oxychloride, hafnium tetrachloride, hafnium oxide, and the like.

Among these Lewis acid catalysts, titanium-containing catalysts, tin-containing catalysts, zirconium-containing catalysts, antimony-containing catalysts and germanium-containing catalysts are preferable in view of reactivity. More specifically, the following compounds are preferable: titanium tetraisopropoxide, titanium tetra-n-butoxide, monobutyltin mono(2-ethylhexanoate), monobutyltin tris(2-ethylhexanoate), stannous 2-ethylhexanoate, zirconium tetraethoxide, zirconium tetra-n-propoxide, zirconium tetra-n-butoxide, antimony triethoxide, antimony tributoxide, germanium tetra-n-butoxide and germanium tetrachloride.

The Lewis acid catalyst is used in a ratio of 0.00001 to 0.005 mol with respect to one mol of carboxyl groups of the carboxylic acid subjected to esterification reaction. When the Lewis acid catalyst is used in less than 0.00001 mol, not only the reaction requires a long time, but also the productivity is reduced. When the Lewis acid catalyst is used in an amount of more than 0.005 mol, the effect is not improved in proportion to the amount used, and the production cost is increased. Furthermore, this makes it difficult to remove the catalyst from the ester, so that the thermal and oxidative stability of the ester may be deteriorated. When the Lewis acid catalyst is used in an amount in the above range, the amount of the remaining metal derived from the Lewis acid catalyst in the resultant ester is substantially not more than the measurement limit.

Phosphorus-Containing Reducing Agent

Examples of the phosphorus-containing reducing agent used in the present invention include phosphorous acid, hypophosphorous acid and salts thereof. Among these, salts of phosphorous acid and salts of hypophosphorous acids are used preferably. Examples of salts of phosphorous acid and salts of hypophosphorous acid include sodium salts, potassium salts, calcium salts, zinc salts, magnesium salts, barium salts, ammonium salts, and the like. Among these, sodium salts are used preferably.

The phosphorus-containing reducing agent is used in a ratio of 0.0003 to 0.005 mol with respect to one mol of carboxyl groups of the carboxylic acid subjected to esterification reaction. A ratio of 0.001 to 0.003 mol is preferable. When it is less than 0.0003 mol, the effect of improving the thermal and oxidative stability of the resultant ester is insufficient. When the phosphorus-containing reducing agent is used in an amount of more than 0.005 mol, the effect is not improved in proportion to the amount used. Furthermore, this makes it difficult to remove it from the ester, so that the thermal and oxidative stability of the ester may be deteriorated. When the phosphorus-containing reducing agent is used in an amount in the above range, the amount of the remaining phosphorus in the produced ester is substantially not more than the measurement limit.

Method for Producing Ester

Next, a method for producing esters of the present invention will be described. In esterification reaction, usually, the amounts of the carboxylic acid and the alcohol that are used are such that the amount of carboxyl groups of the carboxylic acid is 1.0 to 1.5 equivalents with respect to one equivalent of hydroxyl groups of the alcohol. In order to obtain an ester having a low hydroxyl value, it is necessary to perform an esterification reaction in the presence of excessive carboxylic acid. The equivalent ratio is 1.0 equivalent or more. When it exceeds 1.5 equivalents, removal of the excessive carboxylic acid is required after the reaction, which reduces the productivity.

In the method of the present invention, the carboxylic acid and the alcohol that have been adjusted to a suitable ratio are subjected to esterification reaction in the presence of suitable amounts of the Lewis acid and the phosphorus-containing reducing agent. The reaction is performed usually at 120 to 260° C. for 3 to 15 hours. After the reaction is completed, purification is performed by a method that is generally used by those skilled in the art, such as neutralization with an alkali, adsorption with an adsorbent, steaming, distillation or the like, which can be performed alone or in combination, and thus the ester of the present invention can be obtained. Among these methods for purification, a combination of neutralization with an alkali and adsorption with an adsorbent is preferable in view of the thermal and oxidative stability of the ester.

Examples of the alkali used for neutralization include alkali metal hydroxides such as sodium hydroxide and potassium hydroxide; alkali metal salts such as sodium carbonate, potassium carbonate, and sodium hydrogencarbonate; and ammonium salts such as ammonium carbonate. Among these, sodium hydroxide and potassium hydroxide are preferable. The amount of alkali used for neutralization is 1 to 2 equivalents with respect to 1 equivalent of the acid value of the ester, and the alkali is used in the form of an alkali aqueous solution having a concentration of 5 to 20 wt %.

Examples of the adsorbent include activated clay, acid white clay, activated carbon, zeolite, activated alumina, diatomaceous earth, silicon dioxide, aluminum oxide, magnesium oxide, and silica-alumina-containing synthetic adsorbents. Among these, activated clay and silica-alumina-containing synthetic adsorbents are preferable. A preferable amount of an adsorbent used is 0.1 to 5.0 parts by weight with respect to one part by weight of the produced ester.

In a conventional ester that is produced by the use of Brønsted acids or the like as the catalyst, byproducts and the catalyst cannot be removed completely. On the other hand, in the present invention, an ester from which byproducts, the catalyst, and the reducing agent are almost completely removed can be produced, partly because the Lewis acid catalyst and the phosphorus-containing reducing agent are used in low concentrations. The concentrations of metal derived from the Lewis acid catalyst and phosphorus derived from the reducing agent in the produced ester are not more than the detection limit, and they are substantially not contained in the ester. Esters that have such a property have excellent thermal and oxidative stability and are not colored for a long time, as shown in the examples below.

The esters obtained by the method of the present invention are used for various applications such as ester lubricating base stock for grease, ester lubricating base stock for refrigerating machine oil, or ester lubricating base stock for automotive engine oil.

Ester Lubricating Base Stock for Grease and Grease Compositions Containing the Base Stock Esters used as ester lubricating base stocks for grease are esters obtained from a neopentyl polyol having 2 to 6 hydroxyl groups and a monocarboxylic acid having 5 to 10 carbon atoms, and are produced in the presence of the Lewis acid catalyst in an amount of 0.00001 to 0.005 mol and the phosphorus-containing reducing agent in an amount of 0.0003 to 0.005 mol with respect to one mol of carboxyl groups of the carboxylic acid. The catalyst and the reducing agent are removed to the measurement limit or less in the process of purification and are substantially not contained in the ester. The thus obtained ester has the advantages of having excellent non-coloring properties and excellent thermal and oxidative stability, being hardly volatized (the weight decreasing rate is small) even if it is used for a long time, being not colored (the non-coloring properties are excellent), and producing little sludge compared to conventional esters.

The neopentyl polyol having 2 to 6 hydroxyl groups is used preferably because it provides the produced ester with excellent heat resistance. Preferable examples of the neopentyl polyol having 2 to 6 hydroxyl groups include neopentylglycol, trimethylolpropane, pentaerythritol, dipentaerythritol and the like. Among these, trimethylolpropane, pentaerythritol, and dipentaerythritol are more preferable because of the anti-evaporation properties of the obtained ester at high temperatures. In view of long life of grease, pentaerythritol and dipentaerythritol are particularly preferable.

As mentioned above, a monocarboxylic acid having 5 to 10 carbon atoms is preferably used. It is more preferable that branched monocarboxylic acid is contained in the monocarboxylic acids because it provides the resultant ester with excellent low temperature fluidity. It is preferable that the branched monocarboxylic acid is contained in an amount of 25 wt % or more based on the total amount of the monocarboxylic acid. On the other hand, when the ratio of the branched monocarboxylic acid is too large, the anti-evaporation properties at high temperatures may be deteriorated, so that it is preferable that the ratio of the branched monocarboxylic acid is 75 wt % or less. Therefore, it is preferable that the branched monocarboxylic acid is contained in the monocarboxylic acid in a ratio of 25 to 75 wt %. As the branched monocarboxylic acid having 5 to 10 carbon atoms, branched monocarboxylic acid having 7 or more carbon atoms is preferable in view of the anti-evaporation properties, and branched monocarboxylic acid having 9 or less carbon atoms is preferable in view of the low temperature fluidity. The branched carboxylic acid is preferably α- or β-branched carboxylic acid in view of the heat resistance and the hydrolytic stability, and α-branched carboxylic acid is more preferable. More specifically, the following compounds can be used preferably: 2-methylhexanoic acid, 3-methylhexanoic acid, 4-methylhexanoic acid, 5-methylhexanoic acid, 2,2-dimethylpentanoic acid, 2-ethylpentanoic acid, 3-ethylpentanoic acid, 2-ethylhexanoic acid, 3,5,5-trimethylhexanoic acid, neononanoic acid, and the like.

It is preferable that the acid value of the ester is 0.1 mgKOH/g or less in view of the heat resistance and the hydrolytic stability, and more preferably 0.05 mgKOH/g or less. It is preferable that the hydroxyl value of the ester is 10 mgKOH/g or less in view of the anti-evaporation properties at high temperatures and the low temperature fluidity. When the hydroxyl value exceeds 10 mgKOH/g, the thermal and oxidative stability at high temperature is poor, and a sealing material is expanded when sealing is performed with grease containing the ester.

The grease composition of the present invention comprises a base stock that is the ester mentioned above, a thickener, an antioxidant, and if necessary, additives that are generally used, such as an extreme pressure additive, an anticorrosive additive, a defoaming agent, an antiemulsifier, and the like.

Examples of the thickener include complex soaps such as lithium complex salts, calcium complex salts, aluminum complex salts, and the like; alkaline metal salts or alkaline earth metal salts such as calcium salts, sodium salts, lithium salts, and the like; and urea, terephthalamide, and the like. Among these, lithium complex salts, lithium salts and urea are preferable in view of the heat resistance.

Examples of the antioxidant include phenol antioxidants such as 2,6-di-t-butyl-4-methylphenol, 4,4'-methyl bis(2,6-di-t-butyl-4-methylphenol), and the like; amine antioxidants such as p,p'-dioctyl phenylamine, monooctyl diphenylamine, phenothiazine, 3,7-dioctyl phenothiazine, phenyl-1-naphthylamine, phenyl-2-naphthylamine, alkyiphenyl-1-naphthylamine, alkylphenyl-2-naphthylamine, and the like; zinc dialkyl dithiophosphate, zinc diallyl dithiophosphate, and the like. These antioxidants can be used alone or in combination of two or more.

Ester Lubricating Base Stock for Refrigerating Machine Oil and Working Fluid Composition for Refrigerating Machine Oil Containing the Base Stock Esters used as ester lubricating base stocks for refrigerating machine oil are esters obtained from a neopentyl polyol having 2 to 6 hydroxyl groups and a monocarboxylic acid having 5 to 10 carbon atoms, as in the case of the ester used as ester lubricating base stocks for grease. The esters are produced in the presence of the Lewis acid catalyst in an amount of 0.00001 to 0.005 mol and the phosphorus-containing reducing agent in an amount of 0.0003 to 0.005 mol with respect to one mol of carboxyl groups of the carboxylic acid. The catalyst and the reducing agent are removed to the measurement limit or less in the process of purification and are substantially not contained in the ester. The thus obtained ester has the advantages of having excellent non-coloring properties and excellent thermal and oxidative stability, being not substantially changed in its acid value in the sealed tube tests (described below), and being not colored for a long period of time (i.e., the non-coloring properties are excellent), compared to conventional esters.

The neopentyl polyol having 2 to 6 hydroxyl groups is used preferably because the resultant ester can be provided with excellent heat resistance. Preferable examples of the neopentyl polyol having 2 to 6 hydroxyl groups include neopentylglycol, trimethylolpropane, pentaerythritol, dipentaerythritol and the like.

As mentioned above, a monocarboxylic acid having 5 to 10 carbon atoms is preferably used, and a monocarboxylic acid having 5 to 9 carbon atoms is more preferable. It is preferable that branched monocarboxylic acid is contained in the monocarboxylic acid having 5 to 9 carbon atoms because the resultant ester can be provided with excellent low temperature fluidity and miscibility and solubility with hydrofluorocarbon. It is preferable that the branched monocarboxylic acid is contained in an amount of 50 wt % or more based on the total amount of the monocarboxylic acid, more preferably 60 wt % or more, and even more preferably 70 wt % or more. The branched carboxylic acid is preferably α- or β-branched carboxylic acid in view of the heat resistance and the hydrolytic stability of the resultant ester, and α-branched carboxylic acid is more preferable.

It is preferable that the acid value of the ester used as ester lubricating base stock for refrigerating machine oil is 0.05 mgKOH/g or less, and more preferably 0.01 mgKOH/g or less in view of the heat resistance and the hydrolytic stability. It is preferable that the hydroxyl value is 5 mgKOH/g or less, and more preferably 3 mgKOH/g or less in view of the compatibility with sealing material, the heat resistance and the hydrolytic stability. When the ester of the present invention is used as a base stock for refrigerating machine oil, an increase of the acid value and an increase in color number can be prevented in the sealed tube test (see the examples below).

The working fluid composition for refrigerating machine of the present invention comprises a base stock that is the ester mentioned above, a hydrofluorocarbon, and if necessary, additives that are commonly used by those skilled in the art, such as an antioxidant, an extreme pressure additive, a metal deactivator, a foaming agent, and the like.

In the above composition, when the content ratio of the hydrofluorocarbon is too high, the viscosity of the working fluid composition for refrigerating machine oil is reduced, which may cause poor lubrication. Therefore, the content ratio of the hydrofluorocarbon is preferably 90 wt % or less, more preferably 80 wt % or less. On the other hand, when the content ratio of the hydrofluorocarbon is too low, the refrigerating efficiency may be reduced, so that it is preferable that the content ratio of the hydrofluorocarbon is 10 wt % or more. Therefore, in view of the lubricity and the refrigerating efficiency, the content ratio of the ester lubricating base stock for refrigerating machine oil (i.e., the ester) to the hydrofluorocarbon is preferably 10:90 to 90:10 (weight ratio), more preferably 20:80 to 80:20 (weight ratio). Therefore, in view of the lubricity and the refrigerating efficiency, the content ratio of the ester lubricating base stock for refrigerating machine oil (i.e., the ester) to the hydrofluorocarbon is preferably 10:90 to 90:10 (weight ratio), more preferably 20:80 to 90:10 (weight ratio).

As the hydrofluorocarbon, 1,1,1,2-tetrafluoroethane (HFC134a), pentafluoroethane (HFC125), difluoromethane (HFC32) and the like are preferable. These can be used alone or in combination.

Ester Lubricating Base Stock for Automotive Engine Oil and Composition for Engine Oil Containing the Base Stock Esters used as ester lubricating base stocks for automotive engine oil are esters of a neopentyl polyol having 2 to 4 hydroxyl groups and a monocarboxylic acid having 5 to 12 carbon atoms. The esters are produced in the presence of the Lewis acid catalyst in an amount of 0.00001 to 0.005 mol and the phosphorus-containing reducing agent in an amount of 0.0003 to 0.005 mol with respect to one mol of carboxyl groups of the carboxylic acid. The catalyst and the reducing agent are removed to the measurement limit or less in the process of purification and are substantially not contained in the ester. The thus obtained ester is substantially free from the catalyst and the reducing agent and has the advantages of having excellent non-coloring properties and excellent thermal and oxidative stability, and increasing the stability in the rotary bomb oxidation test (described later) by 10% or more, preferably 20% or more, and more preferably 30% or more.

As the neopentyl polyol having 2 to 4 hydroxyl groups, neopentylglycol, trimethylolpropane, pentaerythritol or the like can be used preferably.

A monocarboxylic acid having 5 to 12 carbon atoms is used preferably because it provides the resultant ester with excellent lubricity and excellent heat resistance. It is preferable that linear carboxylic acid is contained in the monocarboxylic acids in view of the temperature-viscosity characteristics and the lubricity of the resultant ester. It is preferable that the linear carboxylic acid is contained in an amount of 40 wt % or more based on the total amount of the monocarboxylic acids, more preferably 50 wt % or more, and even more preferably 60 wt % or more. When the branched carboxylic acid is used, the branched carboxylic acid is preferably α- or β-branched carboxylic acid in view of the heat resistance and the hydrolytic stability of the resultant ester, and α-branched carboxylic acid is more preferable.

It is preferable that the kinematic viscosity of the ester used as ester lubricating base stock for automotive engine oil at 40° C. is 8 to 50 mm$^2$/s, and more preferably 10 to 40 mm$^2$/s. When the kinematic viscosity is less than 8 mm$^2$/s, the volatized amount of the ester at high temperatures is large, and the lubricity is deteriorated. A kinematic viscosity exceeding 50 mm$^2$/s is not preferable because the power loss due to resistance caused by a high viscosity is too large. The hydroxyl value of the ester is preferably 5 mgKOH/g or less, more preferably 3 mgKOH/g or less. When it exceeds 5 mgKOH/g, the oxidative stability of the ester at high temperatures is poor and the detergency is insufficient.

The composition for automotive engine oil of the present invention comprises a base stock that is the ester mentioned above, an antioxidant, and if necessary, other synthetic lubricants and mineral oils, and additives that are commonly used, such as a detergent-dispersant, a viscosity index improver, an anti-wear additive, an extreme pressure additive, an oiliness agent, an anticorrosive additive, a defoaming agent, and the like.

Examples of the anti-oxidant include phenol antioxidants such as 2,6-di-t-butyl-4-methylphenol, 4,4'-methyl bis(2,6-di-t-butyl-4-methylphenol), and the like; amine antioxidants such as p,p'-dioctyl phenylamine, monooctyl diphenylamine, phenothiazine, 3,7-dioctyl phenothiazine, phenyl-1-naphthylamine, phenyl-2-naphthylamine, alkylphenyl-1-naphthylamine, alkylphenyl-2-naphthylamine, and the like; and zinc dialkyl dithiophosphate, zinc diallyl dithiophosphate, and the like. These antioxidants can be used alone or in combination of two or more.

Examples of the synthetic lubricant and mineral oils include poly-α-olefins, high viscosity index semisynthetic oils, polyalkylene glycols, alkyl benzenes, naphthenic mineral oils, paraffin mineral oils, aromatic mineral oils, polybutene, and the like. Among these, poly-α-olefins and high viscosity index semisynthetic oils are preferable because of good compatibility with sealing material and good temperature-viscosity characteristics. Examples of the anti-wear additive include zinc dithiophosphate, zinc dithiocarbamate, dialkyl polysulfides, triallyl phosphates, trialkyl phosphates, and the like. These additives can be used alone or in combination of two or more.

In this specification, although the characteristics of esters suitable for each application are described, some applications may use a common ester. In this case, the ester used for some applications has the same characteristics as for other applications.

EXAMPLES

Hereinafter, the present invention will be described more specifically by way of examples of producing esters.

The following describes a method for evaluating esters prepared in Examples and Comparative Examples.
(I) Kinematic Viscosity (40° C.), Pour Point, Acid Value, Hydroxyl Value and the Color Number (APHA) of Esters
(1) Kinematic viscosity (40° C.): measured according to JIS K 2283
(2) Pour point: measured according to JIS K 2269
(3) Acid value: measured according to JIS C 2101
(4) Hydroxyl value: measured according to JIS K 0070
(5) Color number (APHA): measured according to JOCS 2.2.1.4-1996
(6) Concentration of elements of catalyst and reducing agent remaining in ester (6.1) Concentration of remaining tin (ppb): measured by atomic absorption spectrophotometry according to JIS K 0121 under the following conditions:
Background correction: Polarizing Zeeman effect method
Atomization: using graphite furnace
Wavelength (nm): 224.6
Slit (nm): 1.3

(6.2) Concentration of remaining titanium (ppb): measured by atomic absorption spectrophotometry according to JIS K 0121 under the following conditions:
Background correction: Polarizing Zeeman effect method
Atomization: using graphite furnace
Wavelength (nm): 364.3
Slit (nm): 0.4

(6.3) Concentration of remaining antimony (ppm): measured by atomic absorption spectrophotometry according to JIS K 0121 under the following conditions:
Background correction: Polarizing Zeeman effect method
Atomization: using graphite furnace
Wavelength (nm): 217.6
Slit (nm): 0.4

(6.4) Concentration of remaining germanium (ppm): measured by atomic absorption spectrophotometry according to JIS K 0121 under the following conditions:
Background correction: Polarizing Zeeman effect method
Atomization: using graphite furnace
Wavelength (nm): 265.2
Slit (nm): 0.4

(6.5) Concentration of remaining zirconium and phosphorus (ppm): measured by an emission spectrochemical analyzer (manufactured by Nihon Bunko Co.) using inductively coupled plasma (ICP) as the light source after a pre-treatment according to JIS K 0102 is performed.

(6.6) Concentration of remaining sulfur (ppm): measured according to JIS K 2541

(6.7) Concentration of remaining nitrogen (ppm): measured by double tube type vaporizing combustion using "Trace Nitrogen Analyzer TN-05" (manufactured by Mitsubishi Kasei Corp)

(6.8) Concentration of remaining aromatic compound (ppm): measured according to JIS K 0115

(II) Heating Test

This test is performed to investigate the thermal and oxidative stability of the obtained esters as ester lubricating base stock for grease. The esters are heated in a high temperature chamber at 180° C. in an air atmosphere for 500 hours, and the weight decreasing rate (%) of the heated esters is measured. Then, the Gardner color number (according to JOCS 2.2.1.3-1996) is measured and the presence or absence of sludge is detected. The weight decreasing rate (%) is calculated such that, taking the weight decreasing rate of each of the examples as 100, the weight decreasing rate of the corresponding comparative example is calculated as a relative value.

(III) Rotary Bomb Oxidation Test (RBOT)

This test is performed to investigate the thermal and oxidative stability of the obtained esters as ester lubricating base stock for automotive engine oil. Fifty grams of ester, 5 g of water and 3 m of copper catalyst coil are put in a vessel, oxygen is injected into the vessel until the inner pressure becomes 620 KPa, and the vessel is sealed. This vessel is put in a thermostatic chamber at 150° C., and is rotated at 100 rpm at an angle of 30 degree, and the time (minutes) (RBOT life time value) until the pressure is reduced to 172 KPa is measured.

(IV) Sealed Tube Test

This test is performed to investigate the thermal and oxidative stability of the obtained esters as ester lubricating base stock for refrigerating machine oil. Ten grams of an ester whose moisture content has been adjusted to 2,000 ppm, 5 g of hydrofluorocarbon R-407C (weight ratio of 1,1,1,2-tetrafluoroethane (HFC134a): pentafluoroethane (HFC125): difluoromethane (HFC32)=52:25:23), and iron, copper, and aluminum, each of which is in the cylindrical form having a diameter of 1.6 mm and a length of 10 mm, are put in a glass tube, and the glass tube is sealed. This is heated at 175° C. for 14 days, and then an increase of the acid value and an increase of the color number (ALPHA) of the ester are measured. Separately, the same test is performed using difluoromethane (HFC32) alone instead of the hydrofluorocarbon R-407C.

Example 1

First, 1200.0 g of (8.81 mol) of pentaerythritol, 884.6 g (7.63 mol) of caproic acid (as a carboxylic acid), 1767.4 g (11.26 mol) of n-nonanoic acid (as a carboxylic acid), 2736.6 g (17.43 mol) of 3,5,5-trimethylhexanoic acid (as a carboxylic acid), 20.6 g (0.07 mol; 0.002 mol with respect to one mol of carboxyl groups of the total of the above carboxylic acids) of titanium tetraisopropoxide and 3.9 g (0.04 mol; 0.001 mol with respect to one mol of carboxyl groups of the carboxylic acids) of sodium hypophosphite were put in a 5 liter four-necked flask provided with a thermometer, a nitrogen inlet tube, a stiffer and a condenser to cause a reaction at 240° C. and an atmospheric pressure under a nitrogen stream while distilling produced water. The reaction was stopped when the hydroxyl value of the generated product (reaction mixture) reached 3 mg OH/g or less.

After the reaction was stopped, unreacted carboxylic acids were removed by distillation under a reduced pressure of 1 kPa. Thus, a crude esterified product was obtained in an amount of 3150.4 g, and the acid value was 3.1 mgKOH/g. Then, a 10% potassium hydroxide aqueous solution that corresponds to 1.5 equivalents of the acid value of this crude esterified product was added thereto, and the mixture was stirred at 90° C. for 30 minutes. This mixture was allowed to stand for 30 minutes and an aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and allowed to stand for 30 minutes, followed by removal of an aqueous layer. This water washing process was repeated three times. Then, the pressure was reduced to 1 kPa at 100° C. for dehydration, followed by an adsorption process in which 32.0 g of Kyowaad 500SH (manufactured by Kyowa Chemical Industry Co., Ltd.) were added. The temperature, the pressure and the time during the adsorption process were 100° C., 1 kPa and three hours, respectively. Then, the resultant mixture was filtrated, and thus an ester having a kinematic viscosity (40° C.) of 52.79 mm$^2$/s, a pour point of −50° C. or less, an acid value of 0.01 mgKOH/g or less, a hydroxyl value of 1.5 mgKOH/g, and a color number (APHA) of 20 was obtained in an amount of 2835.4 g, as a final product. The yield of the ester was 89.6% of the theoretical value.

Example 2

First, 1300.0 g of (9.55 mol) of pentaerythritol, 1369.0 g (11.80 mol) of n-heptanoic acid (as a carboxylic acid), 1246.2 g (8.65 mol) of caprylic acid (as a carboxylic acid), 2719.1 g (18.88 mol) of 2-ethylhexanoic acid (as a carboxylic acid), 13.4 g (0.04 mol; 0.001 mol with respect to one mol of carboxyl groups of the total of the above carboxylic acids) of titanium tetra-n-butoxide and 4.2 g (0.04 mol; 0.001 mol with respect to one mol of carboxyl groups of the carboxylic acids) of sodium hypophosphite were put in a 5 liter four-necked flask provided with a thermometer, a nitrogen inlet tube, a stirrer and a condenser to cause a reaction at 240° C. and an atmospheric pressure under a nitrogen stream while distilling produced water. The reaction was stopped when the hydroxyl value of the generated product (reaction mixture) reached 3 mgKOH/g or less.

After the reaction was stopped, unreacted carboxylic acids were removed by distillation under a reduced pressure of 1 kPa. Thus, a crude esterified product was obtained in an amount of 3124.1 g, and the acid value was 2.1 mgKOH/g. Then, a 10% potassium hydroxide aqueous solution that corresponds to 1.5 equivalents of the acid value of this crude esterified product was added thereto, and the mixture was stirred at 90° C. for 30 minutes. This mixture was allowed to stand for 30 minutes and an aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and allowed to stand for 30 minutes, followed by removal of an aqueous layer. This water washing process was repeated three times. Then, the pressure was reduced to 1 kPa at 100° C. for dehydration, followed by an adsorption process in which 15.0 g of activated clay SA-1 (manufactured by Nihon Kassei Hakudo) and 15.0 g of activated alumina DN-1A (manufactured by Mizusawa Chemical Industries) were added. The temperature, the pressure and the time during the adsorption process were 100° C., 1 kPa and three hours, respectively. Then, the resultant mixture was filtratered, and thus an ester having a kinematic viscosity (40° C.) of 30.34 mm$^2$/s, a pour point of −50° C. or less, an acid value of 0.01 mgKOH/g or less, a hydroxyl value of 1.7 mgKOH/g, and a color number (APHA) of 15 was obtained in an amount of 2811.7 g, as a final product. The yield of the ester was 89.3% of the theoretical value.

Example 3

First, 800.0 g of (5.96 mol) of trimethylolpropane, 391.3 g (2.28 mol) of capric acid (as a carboxylic acid), 2636.3 g (16.69 mol) of 3,5,5,-trimethyl hexanoic acid (as a carboxylic acid), 19.1 g (0.06 mol; 0.003 mol with respect to one mol of carboxyl groups of the total of the above carboxylic acids) of monobutyltin mono(2-ethyl hexanoate) and 5.4 g (0.03 mol; 0.001 mol with respect to one mol of carboxyl groups of the carboxylic acids) of sodium phosphite were put in a 5 liter four-necked flask provided with a thermometer, a nitrogen inlet tube, a stirrer and a condenser to cause a reaction at 240° C. and an atmospheric pressure under a nitrogen stream while distilling produced water. The reaction was stopped when the hydroxyl value of the generated product (reaction mixture) reached 3 mgKOH/g or less.

After the reaction was stopped, unreacted carboxylic acids were removed by distillation under a reduced pressure of 1 kPa. Thus, a crude esterified product was obtained in an amount of 3483.5 g, and the acid value was 4.1 mgKOH/g. Then, a 10% potassium hydroxide aqueous solution that corresponds to 1.5 equivalents of the acid value of this crude esterified product was added thereto, and the mixture was stirred at 90° C. for 30 minutes. This mixture was allowed to stand for 30 minutes and an aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and allowed to stand for 30 minutes, followed by removal of an aqueous layer. This water washing process was repeated three times. Then, the pressure was reduced to 1 kPa at 100° C. for dehydration, followed by an adsorption process in which 15.0 g of Tomita AD300P (manufactured by Tomita Pharmaceutical Co. Ltd.) and 15.0 g of Galleon Earth V2 (manufactured by Mizusawa Chemical Industries) were added. The temperature, the pressure and the time during the adsorption process were 100° C., 1 kPa and three hours, respectively. Then, the resultant mixture was filtratered, and thus an ester having a kinematic viscosity (40° C.) of 69.29 mm$^2$/s, a pour point of −50° C. or less, an acid value of 0.01 mgKOH/g or less, a hydroxyl value of 1.0 mgKOH/g, and a color number (APHA) of 15 was obtained in an amount of 3155.1 g, as a final product. The yield of the ester was 90.6% of the theoretical value.

Example 4

First, 1000.0 g of (7.45 mol) of trimethylolpropane, 1426.8 g (8.30 mol) of capric acid (as a carboxylic acid), 1016.8 g (7.82 mol) of 2-methylhexanoic acid (as a carboxylic acid), 1092.2 g (7.58 mol) of 2-ethylhexanoic acid (as a carboxylic acid), 23.3 g (0.07 mol; 0.003 mol with respect to one mol of carboxyl groups of the total of the above carboxylic acids) of zirconium tetra-n-butoxide and 1.6 g (0.02 mol; 0.001 mol with respect to one mol of carboxyl groups of the carboxylic acids) of hypophosphorous acid were put in a 5 liter four-necked flask provided with a thermometer, a nitrogen inlet tube, a stirrer and a condenser to cause a reaction at 240° C. and an atmospheric pressure under a nitrogen stream while distilling produced water. The reaction was stopped when the hydroxyl value of the generated product (reaction mixture) reached 3 mgKOH/g or less.

After the reaction was stopped, unreacted carboxylic acids were removed by distillation under a reduced pressure of 1 kPa. Thus, a crude esterified product was obtained in an amount of 3005.8 g, and the acid value was 8.1 mgKOH/g. Then, a 10% potassium hydroxide aqueous solution that corresponds to 1.5 equivalents of the acid value of this crude esterified product was added thereto, and the mixture was stirred at 90° C. for 30 minutes. This mixture was allowed to stand for 30 minutes and an aqueous layer was removed, and thus a neutralization process was completed. Then, ion exchanged water was added in an amount of 20 parts by weight with respect to 100 parts by weight of the crude esterified product, and the mixture was stirred at 90° C. for 30 minutes and allowed to stand for 30 minutes, followed by removal of an aqueous layer. This water washing process was repeated three times. Then, the pressure was reduced to 1 kPa at 100° C. for dehydration.

Then, the mixture was distilled at 180° C., a pressure in the range of 0.1 to 3 torr, and a flow rate of 4 mL/min with a Smith type distillatory. Thus, an ester having a kinematic viscosity (40° C.) of 23.19 mm$^2$/s, a pour point of −37.5° C. or less, an acid value of 0.01 mgKOH/g or less, a hydroxyl value of 0.5 mgKOH/g, and a color number (APHA) of 20 was obtained in an amount of 2804.9 g, as a final product. The yield of the ester was 92.4% of the theoretical value.

Table 1 shows the alcohols, the carboxylic acids, catalysts, and the reducing agents used for production of esters in Examples 1 to 4. Table 2 collectively shows the properties of the obtained esters. Table 2 also shows the concentrations of elements of the catalysts and reducing agents remaining in the esters and the results of the heating test. Tables 1 and 2 also show those of Examples 5 to 20 and Comparative Examples 1 to 20 described later.

The esters prepared in Examples 1 to 4 and Examples 5 to 20 described below can be used for various applications, but are particularly suitable for ester lubricating base stock for grease.

Comparative Examples 1 to 4

Esters were produced by performing the same operations as in Examples 1 to 4 using the materials shown in Table 1.

Examples 5 to 20

Esters were produced by performing the same operations as in Example 1 for Examples 5 to 8, as in Example 2 for Examples 9 to 12, as in Example 3 for Examples 13 to 16, and as in Example 4 for Examples 17 to 20, using the materials shown in Table 1.

Comparative Examples 5 to 20

Esters were produced by performing the same operations as in Example 1 for Comparative Examples 5 to 8, as in Example 2 for Comparative Examples 9 to 12, as in Example 3 for Comparative Examples 13 to 16, and as in Example 4 for Comparative Examples 17 to 20, using the materials shown in Table 1.

TABLE 1

| | Alcohol | Carboxylic acid (molar ratio) | Catalyst [mol][a)] | Reducing agent [mol][b)] |
|---|---|---|---|---|
| Example 1 | Pentaerythritol | Caproic acid (21)<br>n-Nonanoic acid (31)<br>3,5,5-Trimethylhexanoic acid (27) | Titanium tetraisopropoxide [0.002] | Sodium hypophosphite [0.001] |
| Com. Ex. 1 | | same as Example 1 | p-Toluenesulfonic acid [0.0025] | Sodium phosphite [0.015] |
| Example 2 | Pentaerythritol | n-Heptanoic acid (30)<br>Caprylic acid (22)<br>2-Ethylhexanoic acid (100) | Titanium tetra-n-butoxide [0.001] | Sodium hypophosphite [0.001] |
| Com. Ex. 2 | | same as Example 2 | Titanium tetra-n-butoxide [0.001] | Sodium hypophosphite [0.02] |
| Example 3 | Trimethylolpropane | Capric acid (12)<br>3,5,5-Trimethylhexanoic acid (88) | Monobutyltin mono-2-ethylhexanoate [0.003] | Sodium phosphite [0.001] |
| Com. Ex. 3 | | same as Example 3 | Monobutyltin mono-2-ethylhexanoate [0.003] | Sodium phosphite [0.00001] |
| Example 4 | Trimethylolpropane | Capric acid (35)<br>2-Methylhexanoic acid (33)<br>2-Ethylhexanoic acid (32) | Zirconium tetra-n-butoxide [0.003] | Hypophosphorus acid [0.001] |
| Com. Ex. 4 | | same as Example 4 | Zirconium tetra-n-butoxide [0.003] | Sodium sulfite [0.002] |
| Example 5 | Pentaerythritol | 2-Ethylhexanoic acid (53)<br>Caprylic acid (40)<br>Capric acid (7) | Stannous 2-ethylhexanoate [0.003] | Sodium hypophosphite [0.001] |
| Com. Ex. 5 | | same as Example 5 | Stannous 2-ethylhexanoate [0.003] | Sodium hypophosphite [0.0001] |
| Example 6 | Pentaerythritol | n-Heptanoic acid (40)<br>2-Ethylhexanoic acid (44)<br>3,5,5-Trimethylhexanoic acid (16) | Monobutyltin tris(2-ethylhexanoate) [0.004] | Sodium hypophosphite [0.003] |
| Com. Ex. 6 | | same as Example 6 | Monobutyltin tris(2-ethylhexanoate) [0.004] | Sodium hyposulfite [0.003] |
| Example 7 | Pentaerythritol | n-Heptanoic acid (34)<br>3,5,5-Trimethylhexanoic acid (66) | Titanium tetra-n-butoxide [0.0025] | Sodium phosphite [0.002] |
| Com. Ex. 7 | | same as Example 7 | p-Toluenesulfonic acid [0.0025] | Sodium phosphite [0.002] |
| Example 8 | Pentaerythritol | n-Heptanoic acid (72)<br>3,5,5-Trimethylhexanoic acid (22)<br>Capric acid (6) | Titanium tetraisopropoxide [0.002]<br>Titanium tetra-n-butoxide [0.002] | Sodium phosphite [0.0015] |
| Com. Ex. 8 | | same as Example 8 | Titanium tetraisopropoxide [0.002]<br>Titanium tetra-n-butoxide [0.002] | Sodium phosphite [0.015] |
| Example 9 | Pentaerythritol | Caprylic acid (50)<br>Capric acid (18)<br>3,5,5-Trimethylhexanoic acid (32) | Monobutyltin mono-2-ethylhexanoate [0.0025] | Hypophosphorous acid [0.001] |
| Com. Ex. 9 | | same as Example 9 | Monobutyltin mono-2-ethylhexanoate [0.0025] | Hypophosphorous acid [0.0001] |
| Example 10 | Pentaerythritol | Capric acid (31)<br>n-Nonanoic acid (41)<br>2-Methylhexanoic acid (28) | Zirconium tetra-n-butoxide [0.004] | Hypophosphorous acid [0.003] |
| Com. Ex. 10 | | same as Example 10 | Zirconium tetra-n-butoxide [0.004] | Sodium sulfite [0.002] |
| Example 11 | Pentaerythritol | Capric acid (21)<br>2-Methylhexanoic acid (41)<br>3,5,5-Trimethylhexanoic acid (38) | Zirconium tetraethoxide [0.002] | Hypophosphorous acid [0.002] |
| Com. Ex. 11 | | same as Example 11 | Sulfuric acid [0.0015] | Sodium phosphite [0.002] |
| Example 12 | Pentaerythritol | n-Heptanoic acid (25)<br>Caprylic acid (25)<br>n-Nonanoic acid (41)<br>3,5,5-Trimethylhexanoic acid (20) | Zirconium tetra-n-propoxide [0.002] | Phosphorous acid [0.0015] |
| Com. Ex. 12 | | same as Example 12 | Zirconium tetra-n-propoxide [0.002] | Phosphorous acid [0.015] |
| Example 13 | Pentaerythritol | n-Heptanoic acid (18)<br>n-Nonanoic acid (41)<br>3,5,5-Trimethylhexanoic acid (41) | Monobutyltin mono-2-ethylhexanoate [0.002] | Phosphorous acid [0.0015] |
| Com. Ex. 13 | | same as Example 13 | Monobutyltin mono-2-ethylhexanoate [0.002] | Sodium phosphite [0.00005] |
| Example 14 | Pentaerythritol | Caproic acid (14)<br>n-Nonanoic acid (49)<br>Capric acid (10)<br>3,5,5-Trimethylhexanoic acid (27) | Monobutyltin tris(2-ethylhexanoate) [0.005] | Phosphorous acid [0.0015] |

TABLE 1-continued

|  | Alcohol | Carboxylic acid (molar ratio) | Catalyst [mol][a] | Reducing agent [mol][b] |
|---|---|---|---|---|
| Com. Ex. 14 |  | same as Example 14 | Monobutyltin tris(2-ethylhexanoate) [0.005] | Potassium sulfite [0.002] |
| Example 15 | Trimethylolpropane | n-Nonanoic acid (29)<br>Capric acid (18)<br>2-Ethylhexanoic acid (53) | Antimony triethoxide [0.002] | Hypophosphorous acid [0.0015] |
| Com. Ex. 15 |  | same as Example 15 | p-Toluenesulfonic acid [0.002] | Sodium phosphite [0.0015] |
| Example 16 | Trimethylolpropane | Caprylic acid (21)<br>n-Nonanoic acid (36)<br>3,5,5-Trimethylhexanoic acid (43) | Antimony tributoxide [0.001] | Hypophosphorous acid [0.0015] |
| Com. Ex. 16 |  | same as Example 16 | Antimony tributoxide [0.001] | Sodium phosphite [0.015] |
| Example 17 | Trimethylolpropane | Caprylic acid (10)<br>2-Ethylhexanoic acid (34)<br>3,5,5-Trimethylhexanoic acid (56) | Germanium tetra-n-butoxide [0.002] | Hypophosphorous acid [0.0015] |
| Com. Ex. 17 |  | same as Example 17 | Germanium tetra-n-butoxide [0.002] | Sodium phosphite [0.00002] |
| Example 18 | Dipentaerythritol | Valeric acid (100) | Germanium tetrachloride [0.0005] | Phosphorous acid [0.0015] |
| Com. Ex. 18 |  | same as Example 18 | Germanium tetrachloride [0.0005] | Sodium sulfite [0.0005] |
| Example 19 | Dipentaerythritol | Caproic acid (100) | Antimony triethoxide [0.001] | Phosphorous acid [0.0015] |
| Com. Ex. 19 |  | same as Example 19 | p-Toluenesulfonic acid [0.001] | Sodium phosphite [0.0015] |
| Example 20 | Dipentaerythritol | n-Heptanoic acid (100) | Antimony tributoxide [0.003] | Phosphorous acid [0.0015] |
| Com. Ex. 20 |  | same as Example 20 | Antimony tributoxide [0.003] | Sodium phosphite [0.02] |

[a] Mols per mol of carboxyl groups in carboxylic acids
[b] Mols per mol of carboxyl groups in carboxylic acids

TABLE 2

| | Properties of esters | | | | | | | | | | | Heating test | | |
|---|---|---|---|---|---|---|---|---|---|---|---|---|---|---|
| | Kinematic viscosity | Pour | APHA | Acid | Hydroxyl | Elements[1] | | | | | | Weight decreasing | | Gardner |
| | 40° C. mm²/s | point ° C. | color number | value | value mg KOH/g | Sn | Ti | Sb | Ge | Zr | S | P | rate % | Relative value | color number | Sludge[2] |
| Example 1 | 45.79 | -50> | 20 | 0.01> | 1.5 | 5> | | | | | | 0.1> | 20.5 | 100 | 9 | ○ |
| Com. Ex. 1 | 45.67 | -50> | 410 | 0.01> | 1.4 | | | | | | 74 | 16 | 21.2 | 103 | ≧20 | × |
| Example 2 | 33.34 | -50> | 15 | 0.01> | 1.6 | 5> | | | | | | 0.1> | 24.4 | 100 | 8 | ○ |
| Com. Ex. 2 | 33.39 | -50> | 20 | 0.01> | 2.2 | 5> | | | | | | 21 | 26.7 | 109 | 9 | × |
| Example 3 | 69.29 | -50> | 15 | 0.01> | 2.1 | | | | 1> | | | 0.1> | 22.7 | 100 | 8 | ○ |
| Com. Ex. 3 | 69.26 | -50> | 70 | 0.01> | 2.8 | | | | 1> | | | 0.1> | 24.6 | 108 | 11 | ○ |
| Example 4 | 27.19 | -37.5 | 20 | 0.01> | 2.9 | | | | 1> | | | 0.1> | 25.7 | 100 | 9 | ○ |
| Com. Ex. 4 | 27.22 | -37.5 | 280 | 0.01> | 2.0 | | | | 1> | | 22 | | 27.5 | 107 | ≧20 | × |
| Example 5 | 33.42 | -50> | 15 | 0.01> | 2.1 | 5> | | | | | | 2 | 23.2 | 100 | 8 | ○ |
| Com. Ex. 5 | 33.81 | -50> | 70 | 0.01> | 2.8 | 5> | | | | | | 1 | 26.8 | 116 | 12 | × |
| Example 6 | 35.15 | -50> | 20 | 0.01> | 0.9 | 5> | | | | | | 3 | 26.7 | 100 | 9 | ○ |
| Com. Ex. 6 | 35.26 | -50> | 250 | 0.01> | 1.0 | 5> | | | | | 29 | | 30.5 | 114 | ≧20 | × |
| Example 7 | 57.16 | -50> | 15 | 0.01> | 1.6 | | 5> | | | | | 3 | 22.4 | 100 | 9 | ○ |
| Com. Ex. 7 | 57.03 | -50> | 20 | 0.01> | 0.2 | | | | | 550 | | 3 | 26.7 | 119 | 19 | × |
| Example 8 | 34.63 | -50> | 20 | 0.01> | 2.1 | 5> | | | | | | 2 | 28.7 | 100 | 8 | ○ |
| Com. Ex. 8 | 34.22 | -50> | 20 | 0.01> | 1.8 | 5> | | | | | | 21 | 30.6 | 107 | 18 | × |
| Example 9 | 39.82 | -40 | 20 | 0.01> | 1.0 | 5> | | | | | | 0.1> | 22.7 | 100 | 9 | ○ |
| Com. Ex. 9 | 39.74 | -40 | 120 | 0.01> | 1.2 | 5> | | | | | | 0.1> | 26.5 | 117 | 17 | × |
| Example 10 | 33.41 | -32.5 | 15 | 0.01> | 1.7 | | | | 1> | | | 0.1> | 22.4 | 100 | 8 | ○ |
| Com. Ex. 10 | 33.39 | -32.5 | 350 | 0.01> | 1.9 | | | | 1> | | 51 | | 25.2 | 113 | ≧20 | × |
| Example 11 | 42.44 | -50> | 15 | 0.01> | 2.1 | | | | 1> | | | 0.1> | 25.7 | 100 | 9 | ○ |
| Com. Ex. 11 | 42.29 | -50> | 260 | 0.01> | 1.8 | | | | | 450 | | 0.1> | 28.6 | 111 | ≧20 | × |
| Example 12 | 33.49 | -50> | 20 | 0.01> | 0.8 | | | | 1> | | | 0.1> | 24.2 | 100 | 7 | ○ |
| Com. Ex. 12 | 33.54 | -50> | 15 | 0.01> | 1.0 | | | | 1> | | | 15 | 28.5 | 118 | 7 | × |
| Example 13 | 43.74 | -50> | 15 | 0.01> | 1.5 | 5> | | | | | | 0.1> | 21.4 | 100 | 9 | ○ |
| Com. Ex. 13 | 43.56 | -50> | 80 | 0.01> | 1.2 | 5> | | | | | | 0.1> | 23.7 | 111 | 16 | × |
| Example 14 | 38.06 | -50> | 15 | 0.01> | 2.4 | 5> | | | | | | 0.1> | 24.7 | 100 | 9 | ○ |
| Com. Ex. 14 | 38.12 | -50> | 310 | 0.01> | 2.9 | 5> | | | | | | 21 | 26.6 | 108 | ≧20 | × |
| Example 15 | 27.77 | -50> | 15 | 0.01> | 2.6 | | | 10> | | | | 0.1> | 24.5 | 100 | 9 | ○ |
| Com. Ex. 15 | 27.33 | -50> | 20 | 0.01> | 2.2 | | | | | | 170 | 0.1> | 27.4 | 112 | ≧20 | × |
| Example 16 | 36.59 | -50> | 20 | 0.01> | 2.8 | | | 10> | | | | 0.1> | 21.7 | 100 | 8 | ○ |
| Com. Ex. 16 | 36.51 | -50> | 20 | 0.01> | 2.6 | | | 10> | | | | 19 | 24.8 | 114 | 10 | × |
| Example 17 | 46.82 | -50> | 20 | 0.01> | 1.9 | | | | 5> | | | 0.1> | 24.1 | 100 | 9 | ○ |
| Com. Ex. 17 | 46.79 | -50> | 110 | 0.01> | 1.8 | | | | 5> | | | 0.1> | 26.5 | 110 | 1 | × |
| Example 18 | 50.49 | -50> | 15 | 0.01> | 1.5 | | | | 5> | | | 0.1> | 22.6 | 100 | 9 | ○ |
| Com. Ex. 18 | 50.44 | -50> | 380 | 0.01> | 1.3 | | | | 5> | | 21 | | 26.1 | 115 | ≧20 | × |
| Example 19 | 53.78 | -40 | 20 | 0.01> | 2.1 | | | 10> | | | | 0.1> | 21.5 | 100 | 8 | ○ |
| Com. Ex. 19 | 53.48 | -40 | 20 | 0.01> | 1.8 | | | | | | 140 | 0.1> | 24.9 | 116 | 14 | ○ |
| Example 20 | 57.54 | -50> | 20 | 0.01> | 0.9 | | | 10> | | | | 0.1> | 19.8 | 100 | 9 | ○ |
| Com. Ex. 20 | 57.58 | -50> | 20 | 0.01> | 1.0 | | | 10> | | | 26 | | 21.2 | 107 | 17 | ○ |

[1] Elements of catalyst and reducing agent remaining in ester

TABLE 2-continued

| | Properties of esters | | | | | | | | | | | Heating test | | | |
|---|---|---|---|---|---|---|---|---|---|---|---|---|---|---|---|
| | Kinematic viscosity 40° C. mm²/s | Pour point ° C. | APHA color number | Acid value mg KOH/g | Hydroxyl value | Elements[1] | | | | | | Weight decreasing rate % | Gardner | | Sludge[2] |
| | | | | | | Sn Ti Sb Ge Zr ppb | | | | | S P ppm | | | Relative value | color number | |

[2]Sludge: ○ Absence of sludge
× Presence of sludge

As seen from the results above, the esters prepared in Examples 1 to 20 have a small weight decreasing rate, a small degree of deterioration in the color number (Gardner), and no sludge in the heating test. On the other hand, in Comparative Examples 1, 7, 11, 15 and 19, p-toluenesulfonic acid or sulfuric acid are used as a Brønsted acid catalyst, so that a large amount of sulfur remained in the produced esters. In these comparative examples, sludge was produced or the ester was colored considerably in the heating test, which may be caused by the large amount of the remaining sulfur, which is not clear. In Comparative Examples 2, 8, 12, 16, and 20, the amount of the reducing agent is large, so that sludge was produced or the ester was colored considerably when the heating test was performed with the obtained esters. In Comparative Examples 3, 5, 9, 13, and 17, the amount of the reducing agent was far smaller than that in the range of the present invention, so that sludge was produced or the ester was colored considerably when the heating test was performed with the obtained esters. Since in Comparative Examples 4, 6, 10, 14 and 18, a sulfuric acid-type reducing agent was used in place of a phosphorus-containing reducing agent, the color number of the produced ester was large. Furthermore, sludge was produced and the ester was colored considerably in the heating test. In this way, all the esters obtained in Comparative Examples 1 to 20 have a large weight decreasing rate, the esters were colored considerably (according to the Gardner color number) and sludge was produced in the heating test.

Examples 21 to 40

Esters were produced by performing the same operations as in Example 1 for Examples 21 to 25, as in Example 2 for Examples 26 to 30, as in Example 3 for Examples 31 to 35, and as in Example 4 for Examples 36 to 40, using the materials shown in Table 3. Table 4 collectively shows the properties of the obtained esters. Table 4 also shows the concentrations of elements of the catalysts and reducing agents remaining in the esters and the results of the rotary bomb oxidation test (RBOT). Tables 3 and 4 also show those of Comparative Examples 21 to 40 described later.

The esters prepared in these examples can be used for various applications, but are particularly suitable for ester lubricating base stock for automotive engine oil.

Comparative Examples 21 to 40

Esters were produced by performing the same operations as in Example 1 for Comparative Examples 21 to 25, as in Example 2 for Comparative Examples 26 to 30, as in Example 3 for Comparative Examples 31 to 35, and as in Example 4 for Comparative Examples 36 to 40, using the materials shown in Table 3.

TABLE 3

| | Alcohol | Carboxylic acid (molar ratio) | Catalyst [mol][a] | Reducing agent [mol][b] |
|---|---|---|---|---|
| Example 21 | Trimethylolpropane | Caprylic acid (55)<br>Capric acid (45) | Titanium tetraisopropoxide [0.003] | Sodium hypophosphite [0.003] |
| Com. Ex. 21 | | same as Example 21 | Titanium tetraisopropoxide [0.003] | Sodium sulfite [0.003] |
| Example 22 | Trimethylolpropane | Capric acid (100) | Monobutyltin mono-2-ethylhexanoate [0.002] | Sodium hypophosphite [0.001]<br>Sodium phosphite [0.001] |
| Com. Ex. 22 | | same as Example 22 | Monobutyltin mono-2-ethylhexanoate [0.002] | 2,6-Di-t-butylphenol [0.002] |
| Example 23 | Trimethylolpropane | Caproic acid (11)<br>Caprylic acid (43)<br>Capric acid (46) . | Stannous 2-ethylhexanoate [0.0025] | Sodium phosphite [0.0025] |
| Com. Ex. 23 | | same as Example 23 | p-Toluenesulfonic acid [0.0025] | Sodium phosphite [0.0025] |
| Example 24 | Pentaerythritol | Valeric acid (100) | Monobutyltin tris(2-ethylhexanoate) [0.004] | Sodium phosphite [0.002] |
| Com. Ex. 24 | | same as Example 24 | Methanesulfonic acid [0.004] | Sodium phosphite [0.002] |
| Example 25 | Trimethylolpropane | Valeric acid (18)<br>Caprylic acid (46)<br>Capric acid (36) | Zirconium tetraethoxide [0.003] | Hypophosphorous acid [0.003] |
| Com. Ex. 25 | | same as Example 25 | Zirconium tetraethoxide [0.003] | Sodium sulfite [0.0003] |
| Example 26 | Trimethylolpropane | Valeric acid (13)<br>n-Heptanoic acid (35)<br>Caprylic acid (32)<br>Lauric acid (20) | Zirconium tetra-n-propoxide [0.002] | Hypophosphorous acid [0.001] |
| Com. Ex. 26 | | same as Example 26 | Zirconium tetra-n-propoxide [0.002] | 2,6-Di-t-butylphenol [0.002] |
| Example 27 | Trimethylolpropane | Caproic acid (24)<br>Caprylic acid (28)<br>Capric acid (48) | Titanium tetra-n-butoxide [0.0025] | Hypophosphorous acid [0.0025] |
| Com. Ex. 27 | | same as Example 27 | p-Toluenesulfonic acid [0.0025] | Sodium phosphite [0.0025] |
| Example 28 | Trimethylolpropane | Valeric acid (17) | Zirconium tetra-n-butoxide [0.004] | Phosphorous acid [0.002] |

TABLE 3-continued

| | Alcohol | Carboxylic acid (molar ratio) | Catalyst [mol][a] | Reducing agent [mol][b] |
|---|---|---|---|---|
| Com. Ex. 28 | | n-Nonanoic acid (42)<br>Capric acid (27)<br>Lauric acid (12)<br>same as Example 28 | Methanesulfonic acid [0.004] | Sodium phosphite [0.002] |
| Example 29 | Trimethylolpropane | Caproic acid (18)<br>Caprylic acid (38)<br>Capric acid (34)<br>Lauric acid (10) | Zirconium tetraethoxide [0.002] | Sodium phosphite [0.005] |
| Com. Ex. 29 | | same as Example 29 | Zirconium tetraethoxide [0.002] | Dibutylhydroxytoluene [0.002] |
| Example 30 | Trimethylolpropane | Caproic acid (8)<br>n-Heptanoic acid (15)<br>Caprylic acid (35)<br>Capric acid (42) | Zirconium tetra-n-propoxide [0.0025] | Phosphorous acid [0.0025] |
| Com. Ex. 30 | | same as Example 30 | Zirconium tetra-n-propoxide [0.0025] | Butylhydroxyanisole [0.001] |
| Example 31 | Trimethylolpropane | Caproic acid (24)<br>n-Heptanoic acid (38)<br>n-Nonanoic acid (30)<br>Myristic acid (8) | Monobutyltin mono-2-ethylhexanoate [0.004] | Sodium hypophosphite [0.002] |
| Com. Ex. 31 | | same as Example 31 | p-Toluenesulfonic acid [0.004] | Sodium phosphite [0.002] |
| Example 32 | Neopentylglycol | Caproic acid (10)<br>Caprylic acid (45)<br>Lauric acid (45) | Monobutyltin tris(2-ethylhexanoate) [0.002] | Sodium hypophosphite [0.001] |
| Com. Ex. 32 | | same as Example 32 | Methanesulfonic acid [0.002] | Sodium hypophosphite [0.001] |
| Example 33 | Neopentylglycol | n-Nonanoic acid (100) | Titanium tetraisopropoxide [0.0025] | Sodium phosphite [0.0025] |
| Com. Ex. 33 | | same as Example 33 | Titanium tetraisopropoxide [0.0025] | Sodium sulfite [0.001] |
| Example 34 | Pentaerythritol | Valeric acid (8)<br>Caproic acid (72)<br>n-Heptanoic acid (20) | Titanium tetra-n-butoxide [0.004] | Sodium phosphite [0.002] |
| Com. Ex. 34 | | same as Example 34 | Titanium tetra-n-butoxide [0.004] | Methylhydroquinone [0.0015] |
| Example 35 | Pentaerythritol | Caproic acid (15)<br>n-Heptanoic acid (64)<br>Caprylic acid (21) | Germanium tetra-n-butoxide [0.002] | Hypophosphorous acid [0.001] |
| Com. Ex. 35 | | same as Example 35 | p-Toluenesulfonic acid [0.0005] | Hypophosphorous acid [0.001] |
| Example 36 | Pentaerythritol | Caproic acid (8)<br>n-Heptanoic acid (42)<br>Caprylic acid (50) | Germanium tetrachloride [0.0025] | Hypophosphorous acid [0.0025] |
| Com. Ex. 36 | | same as Example 36 | Methanesulfonic acid [0.002] | Sodium phosphite [0.0025] |
| Example 37 | Pentaerythritol | n-Heptanoic acid (26)<br>Caprylic acid (41)<br>n-Nonanoic acid (33) | Antimony triethoxide [0.004] | Sodium phosphite [0.002] |
| Com. Ex. 37 | | same as Example 37 | Antimony triethoxide [0.004] | Sodium sulfite [0.0001] |
| Example 38 | Pentaerythritol | n-Heptanoic acid (20)<br>Caprylic acid (62)<br>Capric acid (18) | Antimony tributoxide [0.002] | Phosphorous acid [0.001]<br>Sodium phosphite [0.001] |
| Com. Ex. 38 | | same as Example 38 | Antimony tributoxide [0.002] | 2,6-Di-t-butylphenol [0.0005] |
| Example 39 | Trimethylolpropane | n-Valeric acid (14)<br>Caprioc acid (28)<br>n-Heptanoic acid (23)<br>n-Nonanoic acid (23)<br>2-Methylbutyanoic acid (14) | Germanium tetra-n-butoxide [0.0025] | Phosphorous acid [0.0025] |
| Com. Ex. 39 | | same as Example 39 | Sulfuric acid [0.0005] | Sodium phosphite [0.0025] |
| Example 40 | Trimethylolpropane | Caprylic acid (48)<br>Neononanoic acid (52) | Germanium tetrachloride [0.004] | Phosphorous acid [0.002] |
| Com. Ex. 40 | | same as Example 40 | Methanesulfonic acid [0.0031] | Sodium phosphite [0.002] |

[a]Mols per mol of carboxyl groups in carboxylic acids
[b]Mols per mol of carboxyl groups in carboxylic acids

TABLE 4

| | Properties of esters | | | | | | | | | | | Rotary bomb oxidation test | |
|---|---|---|---|---|---|---|---|---|---|---|---|---|---|
| | Kinematic viscosity | Pour point | APHA color number | Acid value | Hydroxyl value | Elements or compounds[1] | | | | | | | |
| | 40° C. mm²/s | ° C. | | mgKOH/g | | Sn | Ti | Sb | Ge | Zr | S | P | Arom.[2] | min | Relative value |
| | | | | | | ppb | | | | | ppm | | | |
| Example 21 | 20.16 | −35 | 35 | 0.01> | 2.2 | 5> | | | | | | 2 | | 1060 | 142 |
| Com. Ex. 21 | 20.23 | −35 | 490 | 0.01> | 2.6 | 5> | | | | 31 | | | | 742 | 100 |
| Example 22 | 25.04 | −10 | 25 | 0.01> | 1.9 | 5> | | | | | | 2 | | 1251 | 143 |

TABLE 4-continued

| | Properties of esters | | | | | | | | | | | | | |
|---|---|---|---|---|---|---|---|---|---|---|---|---|---|---|
| | Kinematic viscosity | Pour point | APHA color | Acid value | Hydroxyl value | Elements or compounds[1] | | | | | | | Rotary bomb oxidation test | |
| | 40° C. mm²/s | ° C. | number | mgKOH/g | | Sn | Ti | Sb | Ge | Zr | S | P | Arom.[2] | min | Relative value |
| | | | | | | ppb | | | | | ppm | | | | |
| Com. Ex. 22 | 24.99 | −10 | 110 | 0.01> | 1.6 | 5> | | | | | | 3 | 130 | 875 | 100 |
| Example 23 | 18.21 | −50 | 20 | 0.01> | 2.9 | 5> | | | | | | 3 | | 1180 | 150 |
| Com. Ex. 23 | 19.66 | −50 | 45 | 0.01> | 1.9 | | | | | | 580 | 3 | | 789 | 100 |
| Example 24 | 15.81 | −45 | 25 | 0.01> | 2.1 | 5> | | | | | | 2 | | 1343 | 146 |
| Com. Ex. 24 | 15.72 | −45 | 50 | 0.01> | 2.2 | | | | | | 255 | 2 | | 921 | 100 |
| Example 25 | 13.72 | −30 | 15 | 0.01> | 2.4 | | | | | 1> | | 0.1> | | 1125 | 138 |
| Com. Ex. 25 | 13.79 | −30 | 320 | 0.01> | 2.5 | | | | | 1> | 120 | | | 816 | 100 |
| Example 26 | 20.74 | −30 | 15 | 0.01> | 1.9 | | | | | 1> | | 0.1> | | 1086 | 118 |
| Com. Ex. 26 | 20.81 | −30 | 80 | 0.01> | 2.4 | | | | | 1> | | | 138 | 921 | 100 |
| Example 27 | 18.12 | −25 | 15 | 0.01> | 2.3 | | | 5> | | | | 0.1> | | 1069 | 129 |
| Com. Ex. 27 | 18.21 | −25 | 70 | 0.01> | 2.2 | | | | | | 35 | 0.1> | | 826 | 100 |
| Example 28 | 23.41 | −30 | 25 | 0.01> | 0.8 | | | | 1> | | | 0.1> | | 1267 | 143 |
| Com. Ex. 28 | 23.46 | −30 | 100 | 0.01> | 1.8 | | | | 1> | | 120 | 0.1> | | 887 | 100 |
| Example 29 | 21.22 | −30 | 20 | 0.01> | 2.3 | | | | 1> | | | 0.1> | | 1086 | 127 |
| Com. Ex. 29 | 21.68 | −30 | 70 | 0.01> | 2.1 | | | | 1> | | | | 143 | 856 | 100 |
| Example 30 | 18.87 | −25 | 15 | 0.01> | 2.0 | | | | 1> | | | 0.1> | | 1098 | 127 |
| Com. Ex. 30 | 18.67 | −25 | 90 | 0.01> | 2.3 | | | | 1> | | | 0.1> | 50 | 867 | 100 |
| Example 31 | 11.46 | −40 | 20 | 0.01> | 0.8 | 5> | | | | | | 0.1> | | 1163 | 126 |
| Com. Ex. 31 | 11.32 | −40 | 60 | 0.01> | 0.6 | | | | | | 80 | 0.1> | | 923 | 100 |
| Example 32 | 8.201 | −50> | 20 | 0.01> | 1.1 | 5> | | | | | | 0.1> | | 841 | 113 |
| Com. Ex. 32 | 8.216 | −50> | 80 | 0.01> | 0.9 | | | | | | 45 | 0.1> | | 746 | 100 |
| Example 33 | 8.319 | −50> | 15 | 0.01> | 2.7 | 5> | | | | | | 0.1> | | 826 | 104 |
| Com. Ex. 33 | 8.310 | −50> | 370 | 0.01> | 2.8 | 5> | | | | | 32 | 0.1> | | 798 | 100 |
| Example 34 | 19.22 | −40 | 25 | 0.01> | 2.0 | 5> | | | | | | 0.1> | | 1069 | 110 |
| Com. Ex. 34 | 19.29 | −40 | 60 | 0.01> | 2.5 | 5> | | | | | | 0.1> | 27 | 968 | 100 |
| Example 35 | 20.91 | −40 | 20 | 0.01> | 2.1 | | 5> | | | | | 0.1> | | 1128 | 124 |
| Com. Ex. 35 | 20.93 | −40 | 60 | 0.01> | 2.6 | | | | | | 52 | 0.1> | | 921 | 100 |
| Example 36 | 22.35 | −40 | 20 | 0.01> | 1.6 | | 5> | | | | | 0.1> | | 1123 | 115 |
| Com. Ex. 36 | 20.30 | −40 | 90 | 0.01> | 1.8 | | | | | | 62 | 0.1> | | 979 | 100 |
| Example 37 | 26.83 | −45 | 15 | 0.01> | 2.1 | | 10> | | | | | 0.1> | | 1006 | 109 |
| Com. Ex. 37 | 26.85 | −45 | 320 | 0.01> | 1.9 | | 10> | | | | 18 | 0.1> | | 926 | 100 |
| Example 38 | 29.82 | −35 | 20 | 0.01> | 2.6 | | 10> | | | | | 0.1> | | 1026 | 113 |
| Com. Ex. 38 | 29.88 | −35 | 80 | 0.01> | 1.6 | | 10> | | | | | 0.1> | 31 | 905 | 100 |
| Example 39 | 24.19 | −50> | 15 | 0.01> | 1.3 | | | 5> | | | | 0.1> | | 1039 | 110 |
| Com. Ex. 39 | 24.68 | −50> | 380 | 0.01> | 1.2 | | | | | | 22 | 0.1> | | 946 | 100 |
| Example 40 | 80.56 | −20 | 25 | 0.01> | 1.4 | | | 5> | | | | 0.1> | | 1036 | 112 |
| Com. Ex. 40 | 80.51 | −20 | 90 | 0.01> | 1.6 | | | | | | 84 | 0.1> | | 923 | 100 |

[1]Elements or compounds of catalyst or reducing agent remaining in ester
[2]Aromatic compounds As seen from the results above, the esters prepared in Examples 21 to 40 have a larger RBOT life time value in the rotary bomb oxidation test than those of the corresponding comparative examples, that is to say, have better thermal and oxidative stability. On the other hand, in Comparative Examples 21, 25, 33, and 37, a sulfuric acid-type reducing agent was used in place of a phosphorus-containing reducing agent, so that the color number of the produced ester itself was large. In Comparative Examples 22, 26, 29, 30, 34 and 38, a phenol-type reducing agent was used in place of a phosphorus-containing reducing agent, so that a phenol compound (aromatic compound) remained in the produced ester. Therefore, the color number of the ester itself was large, and the thermal and oxidative stability was poor. In Comparative Examples 23, 27, 31, 35, and 39, a Brφnsted acid catalyst was used in place of a Lewis acid catalyst, so that a large amount of sulfur remained in the produced esters, and the color number of the esters was large, which may be caused by the large amount of remaining sulfur. The thermal and oxidative stability was also poor. Also in Comparative Examples 24, 28, 32, 36, and 40, methane-sulfonic acid was used as a Brφnsted acid catalyst in place of a Lewis acid catalyst, so that the color number of the produced esters was large, and the thermal and oxidative stability was also poor. Thus, all the esters of Comparative Examples 21 to 40 have large color number and poor results of the rotary bomb oxidation test, compared to the present invention.

Examples 41 to 60

Esters were produced by performing the same operations as in Example 1 for Examples 41 to 46 and 48 to 50 and as in Example 2 for Examples 51 to 60 using the materials shown in Table 5. In Example 47, the same reaction operation was performed as in Example 1 so that a crude esterified product was obtained. Then, a neutralization process was performed, where toluene was added in an amount of 10 parts by weight with respect to 100 parts by weight of the crude esterified product. The water washing process was performed three times as well, and the pressure was reduced to 1 kPa at 150° C. for dehydration and the toluene was removed. Then, the absorption treatment was performed in the same manner as in Example 1, and thus an ester was obtained.

Table 6 collectively shows the properties of the obtained esters. Table 6 also shows the concentrations of elements of the catalysts and reducing agents remained in the esters and the results of the sealed tube test. Tables 5 and 6 also show those of Comparative Examples 41 to 60 described later.

The esters prepared in these examples can be used for various applications, but are particularly suitable for ester lubricating base stock for refrigerating machine oil.

Comparative Examples 41 to 60

Esters were produced by performing the same operations as in Example 1 for Comparative Examples 41 to 50, and as in Example 2 for Comparative Examples 51 to 60 using the materials shown in Table 5.

TABLE 5

| | Alcohol[c] | Carboxylic acid (molar ratio) | Catalyst [mol][a] | Reducing agent [mol][b] |
|---|---|---|---|---|
| Example 41 | Neopentylglycol | 2-Ethylhexanoic acid (100) | Monobutyltin mono-2-ethylhexanoate [0.0015] Titanium tetra-n-butoxide [0.0015] | Sodium hypophosphite [0.003] |
| Com. Ex. 41 | | same as Example 41 | Monobutyltin mono-2-ethylhexanoate [0.0015] Titanium tetra-n-butoxide [0.0015] | Potassium sulfite [0.003] |
| Example 42 | Trimethylolpropane | 2-Methylhexanoic acid (100) | Monobutyltin mono-2-ethylhexanoate [0.004] | Sodium hypophosphite [0.003] |
| Com. Ex. 42 | | same as Example 42 | Monobutyltin mono-2-ethylhexanoate [0.004] | Sodium nitrite [0.003] |
| Example 43 | Pentaerythritol | 2-Ethylhexanoic acid (100) | Stannous 2-ethylhexanoate [0.003] | Sodium hypophosphite [0.001] Sodium phosphite [0.001] |
| Com. Ex. 43 | | same as Example 43 | Stannous 2-ethylhexanoate [0.003] | Sodium hypophosphite [0.01] Sodium phosphite [0.01] |
| Example 44 | Pentaerythritol | 2-Methylhexanoic acid (73) 2-Ethylhexanoic acid (12) 3,5,5-Trimethylhexanoic acid (15) | Titanium tetraisopropoxide [0.003] | Sodium hypophosphite [0.002] |
| Com. Ex. 44 | | same as Example 44 | Titanium tetraisopropoxide [0.003] | Phenyl-α-naphthylamine [0.002] |
| Example 45 | Pentaerythritol | n-Valeric acid (41) n-Heptanoic acid (46) 3,5,5-Trimethylhexanoic acid (13) | Titanium tetra-n-butoxide [0.004] | Sodium hypophosphite [0.002] |
| Com. Ex. 45 | | same as Example 45 | Titanium tetra-n-butoxide [0.004] | 4,4'-Butylidene-bis(6-t-butyl-3-methylphenol) [0.002] |
| Example 46 | Pentaerythritol | 2-Ethylhexanoic acid (40) 3,5,5-Trimethylhexanoic acid (60) | Stannous-2-ethylhexanoate [0.003] | Sodium hypophosphite [0.002] |
| Com. Ex. 46 | | same as Example 46 | p-Toluenesulfonic acid [0.003] | Sodium hypophosphite [0.002] |
| Example 47 | Dipentaerythritol | 2-Ethylhexanoic acid (50) 3,5,5-Trimethylhexanoic acid (50) | Monobutyltin tris(2-ethylhexanoate) [0.003] | Sodium phosphite [0.002] |
| Com. Ex. 47 | | same as Example 47 | Methanesulfonic acid [0.003] | Sodium phosphite [0.002] |
| Example 48 | Pentaerythritol | 2-Methylhexanoic acid (33) 2-Ethylhexanoic acid (67) | Zirconium tetra-n-butoxide [0.0015] | Hypophosphorous acid [0.003] |
| Com. Ex. 48 | | same as Example 48 | Zirconium tetra-n-butoxide [0.00151] | Sodium sulfite [0.003] |
| Example 49 | Pentaerythritol | Valeric acid (21) 3,5,5-Trimethylhexanoic acid (79) | Zirconium tetraethoxide [0.004] | Hypophosphorous acid [0.003] |
| Com. Ex. 49 | | same as Example 49 | Zirconium tetraethoxide [0.004] | Sodium nitrite [0.003] |
| Example 50 | Neopentylglycol (70) Pentaerythritol (30) | Valeric acid (23) 2-Methylhexanoic acid (23) 3,5,5-Trimethylhexanoic acid (54) | Zirconium tetra-n-propoxide [0.003] | Phosphorous acid [0.001] |
| Com. Ex. 50 | | same as Example 50 | Zirconium tetra-n-propoxide [0.003] | Sodium hypophosphite [0.013] |
| Example 51 | Neopentylglycol | Caprylic acid (100) | Antimony triethoxide [0.004] | Hypophosphorous acid [0.003] |
| Com. Ex. 51 | | same as Example 51 | Antimony triethoxide [0.004] | Sodium sulfite [0.0005] |
| Example 52 | Neopentylglycol | 2-Methylhexanoic acid (50) 3,5,5-Trimethylhexanoic acid (50) | Antimony tributoxide [0.003] | Phosphorous acid [0.001] |
| Com. Ex. 52 | | same as Example 52 | Antimony tributoxide [0.003] 3,5,5-trimethylhexanoic acid (50) | Sodium hypophosphite [0.013] |
| Example 53 | Neopentylglycol | 2-Methylhexanoic acid (100) | Germanium tetra-n-butoxide [0.004] | Hypophosphorous acid [0.003] |
| Com. Ex. 53 | | same as Example 52 | Germanium tetra-n-butoxide [0.004] | 2,6-Di-t-butylphenol [0.0005] |
| Example 54 | Neopentylglycol | 3,5,5-Trimethylhexanoic acid (100) | Germanium tetrachloride [0.003] | Phosphorous acid [0.001] |
| Com. Ex. 54 | | same as Example 54 | p-Toluenesulfonic acid [0.003] | Phosphorous acid [0.001] |
| Example 55 | Neopentylglycol | 2-Ethylhexanoic acid (50) 3,5,5-Trimethylhexanoic acid (50) | Zirconium tetra-n-butoxide [0.004] | Hypophosphorous acid [0.003] |
| Com. Ex. 55 | | same as Example 55 | Methanesulfonic acid [0.004] | Hypophosphorous acid [0.003] |
| Example 56 | Trimethylolpropane | 2-Methylhexanoic acid (25) 2-Ethylhexanoic acid (10) 3,5,5-Trimethylhexanoic acid (65) | Zirconium tetraethoxide [0.003] | Phosphorous acid [0.001] |
| Com. Ex. 56 | | same as Example 56 | Zirconium tetraethoxide [0.003] | Sodium nitrite [0.003] |
| Example 57 | Trimethylolpropane | 3,5,5-Trimethylhexanoic acid (100) | Antimony triethoxide [0.004] | Hypophosphorous acid [0.003] |
| Com. Ex. 57 | | same as Example 57 | Antimony triethoxide [0.004] | Phenothiazine [0.001] |
| Example 58 | Trimethylolpropane | 2-Methylhexanoic acid (70) 3,5,5-Trimethylhexanoic acid (30) | Antimony tributoxide [0.003] | Phosphorous acid [0.001] |
| Com. Ex. 58 | | same as Example 58 | Antimony tributoxide [0.003] | t-Butylphenol [0.0005] |
| Example 59 | Pentaerythritol | Valeric acid (50) n-Heptanoic acid (50) | Germanium tetra-n-butoxide [0.004] | Hypophosphorous acid [0.003] |
| Com. Ex. 59 | | same as Example 59 | Germanium tetra-n-butoxide [0.004] | Sodium nitrite [0.003] |
| Example 60 | Neopentyl-glycol (70) Pentaerythritol (30) | Valeric acid (41) n-Heptanoic acid (41) Caprylic acid (18) | Germanium tetrachloride [0.003] | Phosphorous acid [0.001] |

TABLE 5-continued

| | Alcohol[c] | Carboxylic acid (molar ratio) | Catalyst [mol][a] | Reducing agent [mol][b] |
|---|---|---|---|---|
| Com. Ex. 60 | | same as Example 60 | Germanium tetrachloride [0.003] | Monooctyldiphenylamine [0.001] |

[a] Mols per mol of carboxyl groups in carboxylic acids
[b] Mols per mol of carboxyl groups in carboxylic acids
[c] Molar ratio in parenthesis in case when a mixture of alcohols was employed

TABLE 6

| | Properties of esters | | | | | | | | | | | | | |
|---|---|---|---|---|---|---|---|---|---|---|---|---|---|---|
| | Kinematic viscosity 40° C. mm²/s | Pour point ° C. | APHA color number | Acid value mg KOH/g | Hydroxyl value mg KOH/g | Elements or compounds[1] | | | | | | | | Arom.[2] |
| | | | | | | Sn | Ti | Sb | Ge | Zr | S | N | P | |
| | | | | | | ppb | | | | | ppm | | | |
| Example 41 | 7.41 | −50> | 10 | 0.01> | 2.1 | 5> | 5> | | | | | | 0.1> | |
| Com. Ex. 41 | 7.42 | −50> | 250 | 0.01> | 2.3 | 5> | 5> | | | | 36 | | | |
| Example 42 | 15.22 | −50> | 15 | 0.01> | 2.6 | 5> | | | | | | | 0.1> | |
| Com. Ex. 42 | 15.33 | −50> | 280 | 0.01> | 2.9 | 5> | | | | | | 32 | | |
| Example 43 | 45.21 | −5 | 15 | 0.01> | 1.3 | 5> | | | | | | | 0.1> | |
| Com. Ex. 43 | 45.10 | −5 | 15 | 0.01> | 1.9 | 5> | | | | | | | 18 | |
| Example 44 | 31.72 | −50> | 10 | 0.01> | 0.7 | | 5> | | | | | | 0.1> | |
| Com. Ex. 44 | 31.77 | −50> | 70 | 0.01> | 0.3 | | 5> | | | | | | | 126 |
| Example 45 | 67.23 | −40 | 10 | 0.01> | 1.6 | | 5> | | | | | | 0.1> | |
| Com. Ex. 45 | 67.11 | −40 | 55 | 0.01> | 1.4 | | 5> | | | | | | | 940 |
| Example 46 | 75.61 | −35 | 15 | 0.01> | 1.3 | 5> | | | | | | | 0.1> | |
| Com. Ex. 46 | 75.37 | −35 | 70 | 0.01> | 1.9 | | | | | | 560 | | 0.1> | |
| Example 47 | 228.6 | −25 | 20 | 0.01> | 1.7 | 5> | | | | | | | 0.1> | |
| Com. Ex. 47 | 228.1 | −25 | 65 | 0.01> | 0.3 | | | | | | 260 | | | 3 |
| Example 48 | 34.01 | −40 | 15 | 0.01> | 2.2 | | | | | 1> | | | 0.1> | |
| Com. Ex. 48 | 34.15 | −40 | 230 | 0.01> | 2.3 | | | | | 1> | 190 | | | |
| Example 49 | 66.42 | −35 | 15 | 0.01> | 1.1 | | | | | 1> | | | 0.1> | |
| Com. Ex. 49 | 66.47 | −35 | 170 | 0.01> | 1.0 | | | | | 1> | | 24 | | |
| Example 50 | 9.108 | −50> | 20 | 0.01> | 0.8 | | | | | 1> | | | 0.1> | |
| Com. Ex. 50 | 9.113 | −50> | 20 | 0.01> | 0.9 | | | | | 1> | | | | 3 |
| Example 51 | 7.012 | −50> | 20 | 0.01> | 2.2 | | | 10> | | | | | 0.1> | |
| Com. Ex. 51 | 7.018 | −50> | 270 | 0.01> | 1.9 | | | 10> | | | 25 | | | |
| Example 52 | 8.421 | −50> | 20 | 0.01> | 1.2 | | | 10> | | | | | 0.1> | |
| Com. Ex. 52 | 8.412 | −50> | 20 | 0.01> | 0.8 | | | 10> | | | | | | 3 |
| Example 53 | 5.218 | −50> | 15 | 0.01> | 2.1 | | | | 5> | | | | 0.1> | |
| Com. Ex. 53 | 5.210 | −50> | 15 | 0.01> | 2.6 | | | | 5> | | | | | 32 |
| Example 54 | 13.10 | −50> | 15 | 0.01> | 1.9 | | | | 5> | | | | 0.1> | |
| Com. Ex. 54 | 13.09 | −50> | 45 | 0.01> | 1.5 | | | | | | 170 | | 0.1> | |
| Example 55 | 9.701 | −50> | 20 | 0.01> | 1.8 | | | | | 1> | | | 0.1> | |
| Com. Ex. 55 | 9.701 | −50> | 40 | 0.01> | 0.9 | | | | | | 150 | | 0.1> | |
| Example 56 | 32.01 | −50> | 15 | 0.01> | 0.3 | | | | | 1> | | | 0.1> | |
| Com. Ex. 56 | 32.01 | −50> | 110 | 0.01> | 0.1 | | | | | 1> | | 280 | | |
| Example 57 | 51.93 | −50> | 20 | 0.01> | 1.9 | | | 10> | | | | | 0.1> | |
| Com. Ex. 57 | 51.89 | −50> | 55 | 0.01> | 1.3 | | | 10> | | | | 120 | | 58 |
| Example 58 | 21.3 | −50> | 15 | 0.01> | 1.2 | | | 10> | | | | | 0.1> | |
| Com. Ex. 58 | 31.27 | −50> | 80 | 0.01> | 1.3 | | | 10> | | | | | 16 | |
| Example 59 | 17.45 | −50> | 15 | 0.01> | 0.1 | | | | 5> | | | | 0.1> | |
| Com. Ex. 59 | 17.28 | −50> | 240 | 0.01> | 0.3 | | | | 5> | | | 40 | | |
| Example 60 | 15.08 | −50> | 20 | 0.01> | 0.4 | | | | 5> | | | | 0.1> | |
| Com. Ex. 60 | 15.11 | −50> | 60 | 0.01> | 0.7 | | | | 5> | | | 50 | | 395 |

| | Sealed tube test | | | |
|---|---|---|---|---|
| | Hydrofluorocarbon R-407C | | Hydrofluorocarbon HFC32 | |
| | Acid value mg KOH/g | APHA color number | Acid value mg KOH/g | APHA color number |
| Example 41 | 0.01> | 20 | 0.01> | 25 |
| Com. Ex. 41 | 0.15 | 450 | 0.19 | 450 |
| Example 42 | 0.01> | 20 | 0.01> | 25 |
| Com. Ex. 42 | 0.16 | 460 | 0.19 | 480 |
| Example 43 | 0.01> | 20 | 0.01> | 25 |
| Com. Ex. 43 | 0.09 | 190 | 0.1 | 190 |
| Example 44 | 0.01> | 20 | 0.01> | 20 |
| Com. Ex. 44 | 0.08 | 145 | 0.09 | 145 |

TABLE 6-continued

| | | | | |
|---|---|---|---|---|
| Example 45 | 0.01> | 20 | 0.01> | 20 |
| Com. Ex. 45 | 0.42 | 130 | 0.4 | 130 |
| Example 46 | 0.01> | 20 | 0.01> | 20 |
| Com. Ex. 46 | 0.13 | 120 | 0.14 | 130 |
| Example 47 | 0.01> | 25 | 0.01> | 25 |
| Com. Ex. 47 | 0.08 | 110 | 0.12 | 120 |
| Example 48 | 0.04 | 20 | 0.06 | 20 |
| Com. Ex. 48 | 0.12 | 450 | 0.1 | 480 |
| Example 49 | 0.08 | 30 | 0.09 | 30 |
| Com. Ex. 49 | 0.33 | 320 | 0.3 | 360 |
| Example 50 | 0.07 | 65 | 0.07 | 70 |
| Com. Ex. 50 | 0.38 | 110 | 0.32 | 120 |
| Example 51 | 0.57 | 100 | 0.56 | 120 |
| Com. Ex. 51 | 0.74 | 370 | 0.83 | 430 |
| Example 52 | 0.11 | 45 | 0.1 | 45 |
| Com. Ex. 52 | 0.08 | 75 | 0.12 | 90 |
| Example 53 | 0.1 | 50 | 0.09 | 40 |
| Com. Ex. 53 | 0.12 | 140 | 0.1 | 180 |
| Example 54 | 0.12 | 70 | 0.14 | 60 |
| Com. Ex. 54 | 0.32 | 220 | 0.36 | 250 |
| Example 55 | 0.19 | 65 | 0.16 | 70 |
| Com. Ex. 55 | 0.28 | 80 | 0.31 | 90 |
| Example 56 | 0.18 | 50 | 0.11 | 45 |
| Com. Ex. 56 | 0.33 | 210 | 0.34 | 230 |
| Example 57 | 0.23 | 45 | 0.23 | 55 |
| Com. Ex. 57 | 0.48 | 120 | 0.42 | 130 |
| Example 58 | 0.11 | 50 | 0.16 | 50 |
| Com. Ex. 58 | 0.22 | 150 | 0.25 | 180 |
| Example 59 | 0.38 | 50 | 0.39 | 40 |
| Com. Ex. 59 | 0.89 | 450 | 1.2 | 470 |
| Example 60 | 0.25 | 65 | 0.26 | 70 |
| Com. Ex. 60 | 0.77 | 110 | 0.75 | 120 |

[1])Elements or compounds of catalyst or reducing agent remaining in ester
[2])Aromatic compounds As seen from the results above, in the esters prepared in Examples 41 to 60, an increase of the acid value and an increase of the color number in the sealed tube test were suppressed to a low level either for hydrofluorocarbon R-407C (weight ratio of 1,1,1,2-tetrafluoroethane (HFC134a): pentafluoroethane (HFC125): difluoromethane (HFC32)=52:25:23) or difluoromethane (HFC32).

In Comparative Examples 41, 42, 48, 51, 56 and 59, a sulfuric acid-type or a nitric acid-type reducing agent was used in place of a phosphorus-containing reducing agent. Therefore, elements derived from the reducing agent remained in a large amount in the produced ester. In these comparative examples, the color number of the produced ester was large, and the acid value after the test was very high, and the thermal and oxidative stability was poor, which may be caused by the large amount of the remaining elements. In Comparative Examples 43, 50, and 52, a large amount of phosphorus-containing reducing agent was used, so that the phosphorus-containing reducing agent remained in the produced ester in a large amount. Therefore, although the color number of the esters was equal to that of the corresponding examples at the time when the esters were prepared, in the sealed tube test, the color number was increased, the acid value increased, and the thermal and oxidative stability was poor. In Comparative Examples 44, 45, 53, 57, 58 and 60, reducing agents other than the phosphorus-containing reducing agents (aromatic reducing agents) were used, so that the aromatic compound remained in the produced ester. Therefore, the color number was increased, the acid value increased, and the thermal and oxidative stability was very poor in the sealed tube test. In Comparative Examples 46, 47, 54, and 55, p-toluenesulfonic acid or methanesulfonic acid was used as a Brønsted acid catalyst in place of a Lewis acid catalyst, so that a large amount of sulfur remained in the produced ester, and the color number of the produced esters was large. Furthermore, the color number was increased, the acid value increased, and the thermal and oxidative stability was poor in the sealed tube test.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for producing an ester including reacting an alcohol with a carboxylic acid, comprising:

reacting the alcohol with the carboxylic acid in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester.

2. The method of claim 1, wherein the Lewis acid catalyst is at least one selected from the group consisting of titanium-containing Lewis acid catalysts, tin-containing Lewis acid catalysts, antimony-containing Lewis acid catalysts, germanium-containing Lewis acid catalysts, and zirconium-containing Lewis acid catalysts.

3. The method of claim 1, wherein the alcohol is a neopentyl polyol having 2 to 6 hydroxyl groups, and the carboxylic acid is a monocarboxylic acid having 5 to 10 carbon atoms.

4. The method of claim 1, wherein the alcohol is a neopentyl polyol having 2 to 4 hydroxyl groups, and the carboxylic acid is a monocarboxylic acid having 5 to 12 carbon atoms.

5. An ester obtained by a process comprising:

reacting an alcohol with a carboxylic acid in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

6. An ester lubricating base stock for grease obtained by a method comprising:

reacting a neopentyl polyol having 2 to 6 hydroxyl groups with a monocarboxylic acid having 5 to 10 carbon atoms in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

7. An ester lubricating base stock for refrigerating machine oil obtained by a process comprising:

reacting a neopentyl polyol having 2 to 6 hydroxyl groups with a monocarboxylic acid having 5 to 10 carbon atoms in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

8. An ester lubricating base stock for automotive engine oil obtained by a process comprising:

reacting a neopentyl polyol having 2 to 4 hydroxyl groups with a monocarboxylic acid having 5 to 12 carbon atoms in a presence of a Lewis acid catalyst in an amount of 0.00001 to 0.005 mol and a phosphorus-containing reducing agent in an amount of 0.0003 to 0.005 mol with respect to one mol of carboxyl groups of the carboxylic acid, and separating a resultant ester, wherein the acid catalyst and the reducing agent are substantially removed from the resultant ester.

9. A grease composition, wherein the composition comprises the ester lubricating base stock for grease of claim 6, a thickener, and an antioxidant, and wherein the ester lubricating base stock for grease is contained in a ratio of 10 to 90% by weight.

10. A working fluid composition for refrigerating machine oil comprising the ester lubricating base stock for refrigerating machine oil of claim 7 and a hydrofluorocarbon in a weight ratio of 10:90 to 90:10.

11. A composition for engine oil, wherein the composition comprises the ester lubricating base stock for automotive engine oil of claim 8, an anti-wear additive, and an antioxidant, and wherein the ester lubricating base stock for automotive engine oil is contained in a ratio of 5 to 95% by weight.

12. The method of claim 2, wherein the alcohol is a neopentyl polyol having 2 to 6 hydroxyl groups, and the carboxylic acid is a monocarboxylic acid having 5 to 10 carbon atoms.

13. The method of claim 2, wherein the alcohol is a neopentyl poiyoi having 2 to 4 hydroxyl groups, and the carboxylic acid is a monocarboxylic acid having 5 to 12 carbon atoms.

* * * * *

UNITED STATES PATENT AND TRADEMARK OFFICE
CERTIFICATE OF CORRECTION

PATENT NO. : 6,617,289 B2
DATED : September 9, 2003
INVENTOR(S) : Michimasa Memita et al.

It is certified that error appears in the above-identified patent and that said Letters Patent is hereby corrected as shown below:

Column 8,
Line 14, "alkyiphenyl" should read -- alkylphenyl --.

Column 9,
Lines 25-29, delete "Therefore, in view of the lubricity and the refrigerating efficiency, the content ratio of the ester lubricating base stock for refrigerating machine oil (i.e., the ester) to the hydrofluorocarbon is preferably 10:90 to 90:10 (weight ratio), more preferably 20:80 to 90:10 (weight ratio)."

Column 12,
Line 16, "ALPHA" should read -- APHA --.
Line 32, "stiffer" should read -- stirrer --.
Line 35, "3 mg OH/g" should read -- 3mgKOH/g --.
Line 53, "SOOSH" should read -- 500SH --.

Column 21,
Line 50, Table 3 Column 3, "Caprioc" should read -- Caproic --.
Line 53, Table 3 Column 3, "2-Methylbutylnoic" should read -- 2-Methylbutanoic --.
Line 57, Table 3 Column 4, "[0.0031" should read -- [0.003] --.

Columns 21 and 22,
Table 4, the Title "Properties of esters" should be placed over Columns 2-6.

Column 28,
Line 5, Table 6 Column 3, "20" should read -- 25 --.
Line 36, Table 6 Column 14, delete "16"
Line 36, Table 6 Column 15, insert -- 16 --.

Signed and Sealed this

Third Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,617,289 B2
DATED : September 9, 2003
INVENTOR(S) : Memita et al.

It is certified that error appears in the above-identified patent and that said Letters Patent is hereby corrected as shown below:

<u>Column 26,</u>
Table 5, column 4, directly below "Antimony tributoxide [0.003]" and above "Germanium tetra-n-butoxide [0.004]", delete line 45 "3,5,5,-trimethylhexanoic acid (50)".

Signed and Sealed this

Seventh Day of September, 2004

JON W. DUDAS
*Director of the United States Patent and Trademark Office*